US008277474B2

(12) United States Patent
Norman et al.

(10) Patent No.: US 8,277,474 B2
(45) Date of Patent: Oct. 2, 2012

(54) SURGICAL CUTTING INSTRUMENT

(75) Inventors: Gerould W. Norman, Jacksonville, FL (US); Dale E. Slenker, Jacksonville, FL (US); Kenneth M. Adams, Jacksonville, FL (US); John T. Cleveland, Bryceville, FL (US)

(73) Assignee: Medtronic, Inc., Jacksonville, FL (US)

( * ) Notice: Subject to any disclaimer, the term of this patent is extended or adjusted under 35 U.S.C. 154(b) by 1433 days.

(21) Appl. No.: 10/854,020

(22) Filed: May 26, 2004

(65) Prior Publication Data
US 2005/0277970 A1 Dec. 15, 2005

(51) Int. Cl.
*A61B 17/32* (2006.01)
(52) U.S. Cl. .................... 606/171; 606/180
(58) Field of Classification Search .......... 606/180, 606/75, 108, 144, 213, 219, 170, 171; 600/176
See application file for complete search history.

(56) References Cited

U.S. PATENT DOCUMENTS

| 5,286,253 | A | * | 2/1994 | Fucci ............................ 604/22 |
| 5,411,514 | A | * | 5/1995 | Fucci et al. .................. 606/180 |
| 5,591,187 | A | | 1/1997 | Dekel |
| 5,592,727 | A | | 1/1997 | Glowa et al. |
| 5,601,583 | A | * | 2/1997 | Donahue et al. ............. 606/170 |
| 5,620,447 | A | | 4/1997 | Smith et al. |
| 5,669,921 | A | * | 9/1997 | Berman et al. ............... 606/167 |
| 5,769,086 | A | * | 6/1998 | Ritchart et al. .............. 600/566 |
| 5,873,886 | A | * | 2/1999 | Larsen et al. ................. 606/180 |
| 5,910,133 | A | * | 6/1999 | Gould ....................... 604/170.03 |
| 5,916,231 | A | | 6/1999 | Bays |
| 5,921,956 | A | * | 7/1999 | Grinberg et al. ........... 604/95.01 |
| 6,214,009 | B1 | | 4/2001 | Toriumi et al. |
| 6,375,635 | B1 | | 4/2002 | Moutafis et al. |
| 2001/0018553 | A1 | * | 8/2001 | Krattiger et al. ............. 600/173 |
| 2001/0031950 | A1 | * | 10/2001 | Ryan ............................ 604/265 |
| 2003/0181934 | A1 | | 9/2003 | Johnston et al. |

FOREIGN PATENT DOCUMENTS

| JP | 6269459 A | 9/1994 |
| JP | 2003135473 A | 5/2003 |
| JP | 2003299665 A | 10/2003 |

OTHER PUBLICATIONS

Japanese Office Action mailed Aug. 9, 2010 (3 pages).

* cited by examiner

*Primary Examiner* — Katherine Dowe
(74) *Attorney, Agent, or Firm* — Dicke, Billig & Czaja, PLLC

(57) ABSTRACT

A surgical cutting instrument including a first elongated member, a second tubular member, a handpiece, a first hub, a second hub, and an actuator assembly. The first tubular member has cutting tip and is co-axially disposed within the second tubular member such that the cutting tip is exposed at a cutting window. The first hub is mounted to the first tubular member and is moveably coupled to the handpiece. The second hub is mounted to the second tubular member and defines a hub axis. The actuator assembly rotatably couples the second hub to the handpiece and includes an actuator. Movement of the actuator is translated to rotational movement of the second hub so as to effectuate spatial rotation of the cutting window. In this regard, the actuator movement is not co-axial with the hub axis.

38 Claims, 15 Drawing Sheets

SURGICAL CUTTING INSTRUMENT

BACKGROUND

The present invention relates to a surgical cutting instrument. More particularly, it relates to a surgical cutting instrument adapted to facilitate cutting window rotation.

Surgical cutting instruments in which an elongated inner member (i.e., shaft or tube) is rotated within an elongated outer tubular member have become well accepted in surgical procedures where access to the surgical site is gained via a narrow portal or passage. Typically, the outer tubular member includes a distal end forming an opening defining a cutting window or port, and the inner member includes a distal end forming a cutting tip for cutting bodily tissue at the window. Proximal ends of the inner and outer members are commonly secured to hubs that, in turn, are attached to a powered handpiece for rotating and/or oscillating the inner member relative to the outer tubular member. The cutting tip of the inner member can have various configurations specific to the surgical procedure in question (e.g., cutting, resecting, abrading, shaving, etc.), with the cutting window being suitably configured to cooperate with a particular configuration of the cutting tip. Often, the inner member is tubular so that the loose tissue resulting from a cutting, resecting, or abrading procedure can be aspirated through the hollow lumen of the inner member. With specific reference to ENT (i.e., ear, nose, and throat) applications, such as sinus surgery, adenoidectomy, laryngeal surgery, etc., extremely sharp, micro-resecting blades or cutting tips are typically employed to effectuate the desired procedure.

Use of the above-described surgical cutting instruments generally entails delivering the cutting window/cutting tip to the target site and positioning the cutting window such that the cutting tip is "exposed" to the desired tissue. To this end, with conventional surgical cutting instruments, while the inner member, and thus the cutting tip, is rotatable relative to the handpiece, the outer tubular member, and thus the cutting window, is not. That is to say, a rotational or spatial position of the cutting window relative to the handpiece is fixed with most available surgical cutting instruments. As a result, in order to spatially position the cutting window so as to expose the cutting tip to desired tissue, the surgeon must physically move or rotate the handpiece. In many instances, this requires the surgeon to contort his or her hand(s) to an otherwise uncomfortable position. Further, many surgical procedures require that tissue at different spatial locations at a particular target site be acted upon by the cutting tip. Thus, while upon initial placement at the target site the cutting window may be properly oriented for a first portion of the procedure, tissue at a different spatial location will also require removal, in turn requiring that the spatial position of the cutting window be altered or rotated. Once again, with conventional surgical cutting instruments, this procedural specification requires the surgeon to physically change the orientation of the handpiece, thus taxing the surgeon's hand(s) and/or requiring the surgeon to temporarily halt the procedure and move to a different physical position relative to the patient. To accommodate this requirement, handpieces are often configured so that the surgeon can readily grasp the handpiece at a wide variety of rotational orientations. While facilitating this end use, the resultant handpiece is less than ergonomically optimal; that is to say, the resultant handpiece does not conform to a surgeon's hand in any one rotational position.

Where the surgical cutting instrument is used in conjunction with an image guided surgery (IGS) system, additional concerns may arise. In particular, IGS generally entails registering the cutting window/cutting tip once deployed to the target site. Where the cutting window spatial orientation must be changed during the procedure, surgeons will commonly remove the instrument from the patient to more easily re-orientate the handpiece and thus the cutting window. When this is done, and following reinsertion of the cutting instrument, the cutting window/cutting tip must be re-registered relative to the IGS system, thereby extending the surgical procedure time.

The need to remove the surgical cutting instrument during a surgical procedure to effectuate a change in the cutting window spatial orientation is routinely encountered where the surgical cutting instrument includes one or more bends along a longitudinal length thereof. As a point of reference, some surgical cutting instruments, and in particular the outer tubular member thereof, are straight or linear along their longitudinal length. Others are curved in accordance with a specific procedure to facilitate positioning of the cutting tip against expected target site tissue. With the curved or bent configuration, the cutting window will move in an irregular fashion with rotation of the handpiece, effectively rotating about the bend or longitudinal point of curvature. Under these circumstances, then, it is virtually impossible for the surgeon to accurately alter the cutting window position without first removing the surgical cutting instrument from the patient.

Some efforts have been made to address the above concerns. In particular, surgical cutting instruments have been devised having a handpiece design that allows the surgeon to manually rotate the outer tubular member, and thus the cutting window, relative to the handpiece. For example, U.S. Pat. No. 5,620,447 describes one such known instrument. Unfortunately, however, manual operation of these handpiece designs is less than optimal. In particular, known surgical cutting instruments that otherwise facilitate rotation of the cutting window relative to the handpiece require both hands of the surgeon to effectuate rotation of the cutting window. One of the surgeon's hands grasps a base portion of the handpiece, whereas the surgeon's other hand grasps a knob that is otherwise affixed to the outer tubular member (and thus the cutting window). Once properly held, the surgeon then applies a torque to the knob/base by forcibly rotating his/her hands in opposite directions. This two-handed requirement is cumbersome at best, especially where the surgeon is also required to hold an IGS system instrument.

Surgical cutting instruments continue to be extremely useful. However, the inability to readily and conveniently change a rotational orientation of the cutting window at the target site has not been fully addressed. Therefore, a need exists for a surgical cutting instrument capable of effectuating rotation of the cutting window relative to the handpiece without occupying both of the surgeon's hands.

SUMMARY

One aspect of the present invention relates to a surgical cutting instrument including a first elongated member, a second tubular member, a handpiece, a first hub, a second hub, and an actuator drive assembly. The first elongated member has a proximal section and a distal section, with the distal section including a cutting tip. The second tubular member includes a proximal region and a distal region, with the distal region forming a cutting window. The first elongated member is co-axially disposed within the second tubular member such that the cutting tip is exposed at the cutting window. The first hub is mounted to the proximal section of the first elongated member and is moveably coupled to the handpiece. The second hub is mounted to the proximal region of the second tubular member and is rotatably coupled to the handpiece. In this regard, the second hub defines a hub axis. Finally, the actuator assembly rotatably couples the second hub to the handpiece and includes an actuator. With this in mind, the actuator assembly is adapted to translate a movement of the actuator to a rotational movement of the second hub relative to the handpiece so as to effectuate spatial rotation of the cutting window. In this regard, the actuator movement is not co-axial with the hub axis. For example, in one embodiment, the actuator movement is linear, with the actuator assembly translating this linear movement into rotational movement of the second hub relative to the handpiece. In an alternative embodiment, the actuator movement is a rotational movement about a rotational axis that is not co-axial with the hub axis. For example, the rotational axis can be non-parallel to the hub axis, or can be parallel and offset relative to the hub axis.

Another aspect of the present invention relates to a method of endoscopically removing tissue from a target site of a patient by a user having first and second hands. The method includes providing a surgical cutting instrument including a first elongated member having a cutting tip, a second tubular member forming a cutting window, and a handpiece. The first elongated member is co-axially disposed within the second tubular member such that the cutting tip is exposed at the cutting window and combines to define a cutting implement. Further, the tubular members are coupled to the handpiece. The handpiece is grasped by the user's first hand. The surgical cutting instrument is then deployed such that the cutting implement is adjacent the target site with the cutting window positioned at a first spatial orientation relative to the handpiece. The cutting window is rotated relative to the handpiece while the cutting implement is maintained at the target site such that the cutting window is positioned at a second spatial orientation relative to the handpiece. To this end, the user's second hand is not required to effectuate rotation of the cutting window. More particularly, the user's first hand continues to grasp the handpiece, and the user's second hand does not manually apply a rotational force to the surgical instrument. Finally, the first elongated member is moved relative to the second tubular member such that the cutting tip removes tissue from the target site. In one embodiment, rotation of the cutting window is achieved by operating an actuator with the user's first hand while continuing to grasp the handpiece, such as by operating a wheel, slide, or electronic switch disposed on the handpiece. Alternatively, a foot switch is operated to effectuate cutting window rotation.

In another embodiment, the method further comprises use of an image guided surgery (IGS) system and includes positioning a visualization instrument to enable observation of the target site prior to rotation of the cutting window. A position of the cutting implement relative to the target site is registered via the visualization instrument with the cutting window at the first spatial orientation. With this in mind, the step of rotating the cutting window is characterized by maintaining the visual instrument registration during and following positioning of the cutting window at the second spatial orientation.

DETAILED DESCRIPTION

Figure 1:
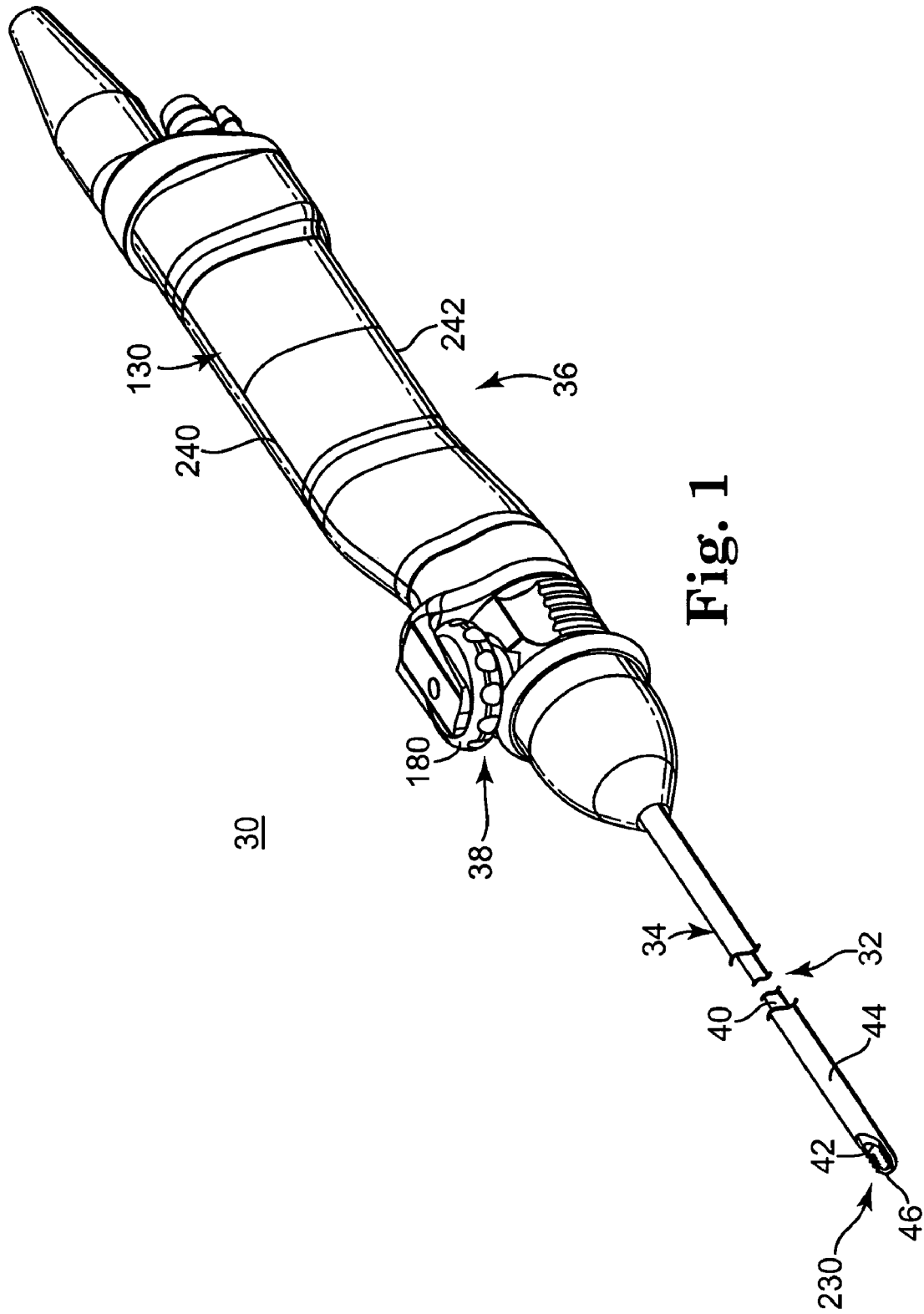
FIG. 1 is a perspective view of one embodiment of a surgical cutting instrument in accordance with the present invention.

One preferred embodiment of a surgical cutting instrument 30 in accordance with the present invention is illustrated in FIG. 1. The surgical cutting instrument 30 includes a first blade member or assembly 32, a second blade member or assembly 34, a handpiece 36, and an actuator assembly 38 (referenced generally in FIG. 1). The components are described in greater detail below. In general terms, however, the first blade assembly 32 includes a first tubular member 40 and a cutting tip 42. The second blade assembly 34 includes a second tubular member 44 forming a cutting window 46. The first tubular member 40 is co-axially disposed within the second tubular member 44 such that the cutting tip 42 is exposed at the cutting window 46. Hubs (not shown) are associated with the first and second blade assemblies 32, 34 and couple the first and second tubular members 40, 44, respectively, to the handpiece 36 such that the tubular members 40, 44 are rotatable relative to one another and the handpiece 36. In this regard, the actuator assembly 38 facilitates rotation of the second tubular member 44, and thus the cutting window 46, relative to the handpiece 36.

A. Blade Assemblies 32, 34

Figure 2:
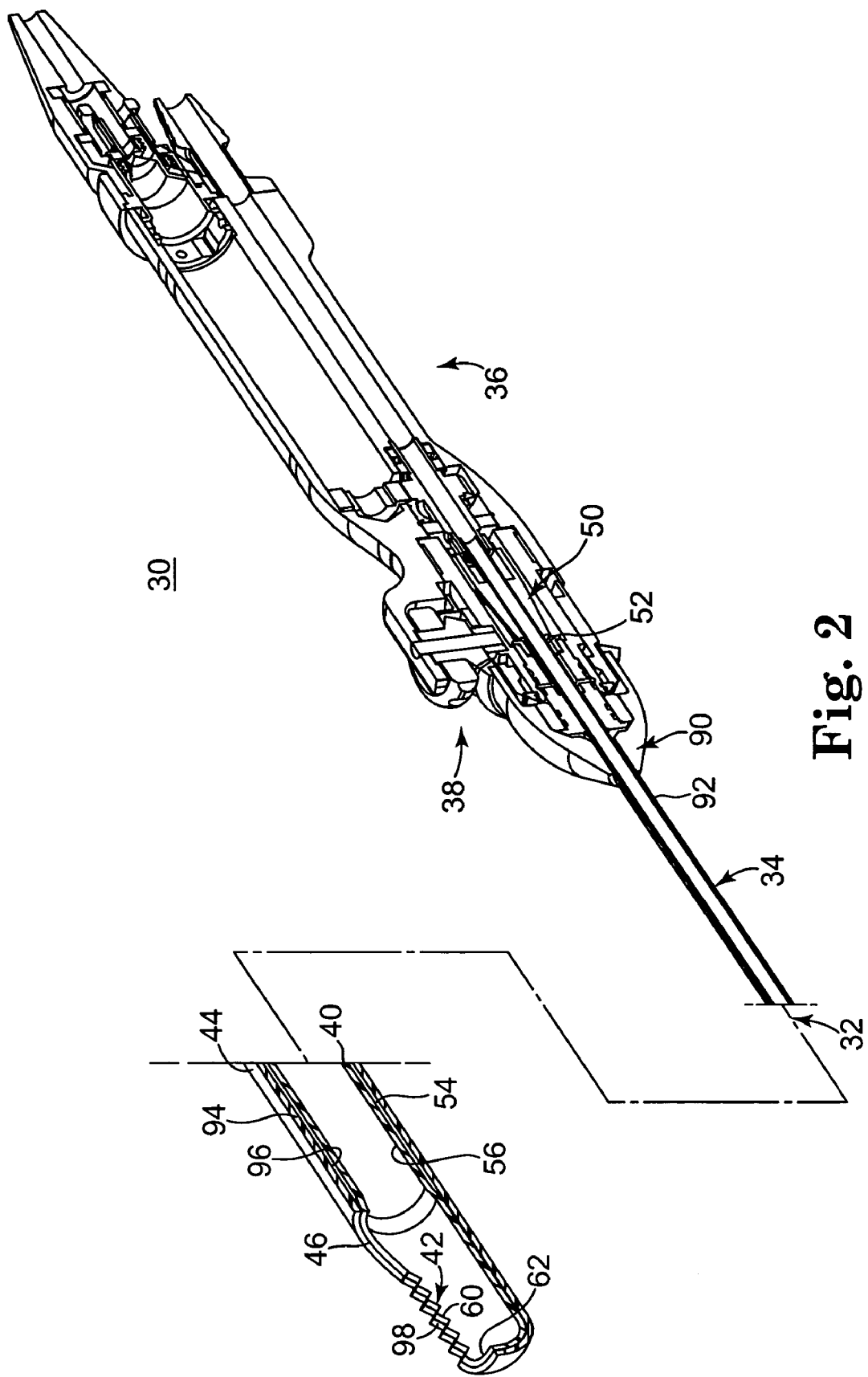
FIG. 2 is a partial cross-sectional view of portions of the instrument of FIG. 1 including distal features thereof shown in an enlarged form.

The first blade assembly 32 is shown in greater detail in FIG. 2 and includes the first tubular member 40, the cutting tip 42, and a first hub 50. Once again, the first hub 50 couples the first tubular member 40 to the handpiece 36 such that the first hub 50, and thus the first tubular member 40, is rotatable relative to the handpiece 36. With this in mind, the first tubular member 40 defines a proximal section 52, a distal section 54, and a central lumen 56 extending therebetween. The distal section 54 forms the cutting tip 42 that is optimally configured to perform a desired cutting procedure as is known in the art, such as resecting or shaving. In one embodiment, the cutting tip 42 defines a serrated edge 60 surrounding an opening 62 that is fluidly connected to the lumen 56. Alternatively, the cutting tip 42 can assume a variety of other forms, such as a bur. With the bur configuration, the first tubular member 40 need not include the central lumen 56 such that the first tubular member 40 is an elongated shaft. Thus, the first tubular member 40 can simply be referred to as an elongated member. Regardless, in one embodiment, the first tubular member 40 is formed of a rigid material, such as 304 stainless steel, and is linear in longitudinal extension. Alternatively, and as described in greater detail below, the first tubular member 40 can be configured to effectuate bending thereof, such as by a flexible coupling (not shown).

The first hub 50 is mounted to the proximal section 52. With additional reference to FIG. 3A that otherwise illustrates the surgical cutting instrument with the tubular members 40, 44 (FIG. 2) removed, the first hub 50 forms a central passage 70 and includes a distal portion 72 and a proximal portion 74. For ease of illustration, not all components are shown with cross-hatching in FIG. 3A. A diameter of the passage 70 at the proximal portion 74 is greater than a diameter at the distal portion 72. In particular, the central passage 70 at the distal portion 72 is sized for mounting to the proximal section 52 of the first tubular member 40. As described in greater detail below, the distal portion 74 is configured for interfacing with a separate drive component, and forms splines 76. Further, the central passage 70 at the proximal portion 74 is sized to maintain a gasket (not shown), such as an O-ring.

Figure 3A:
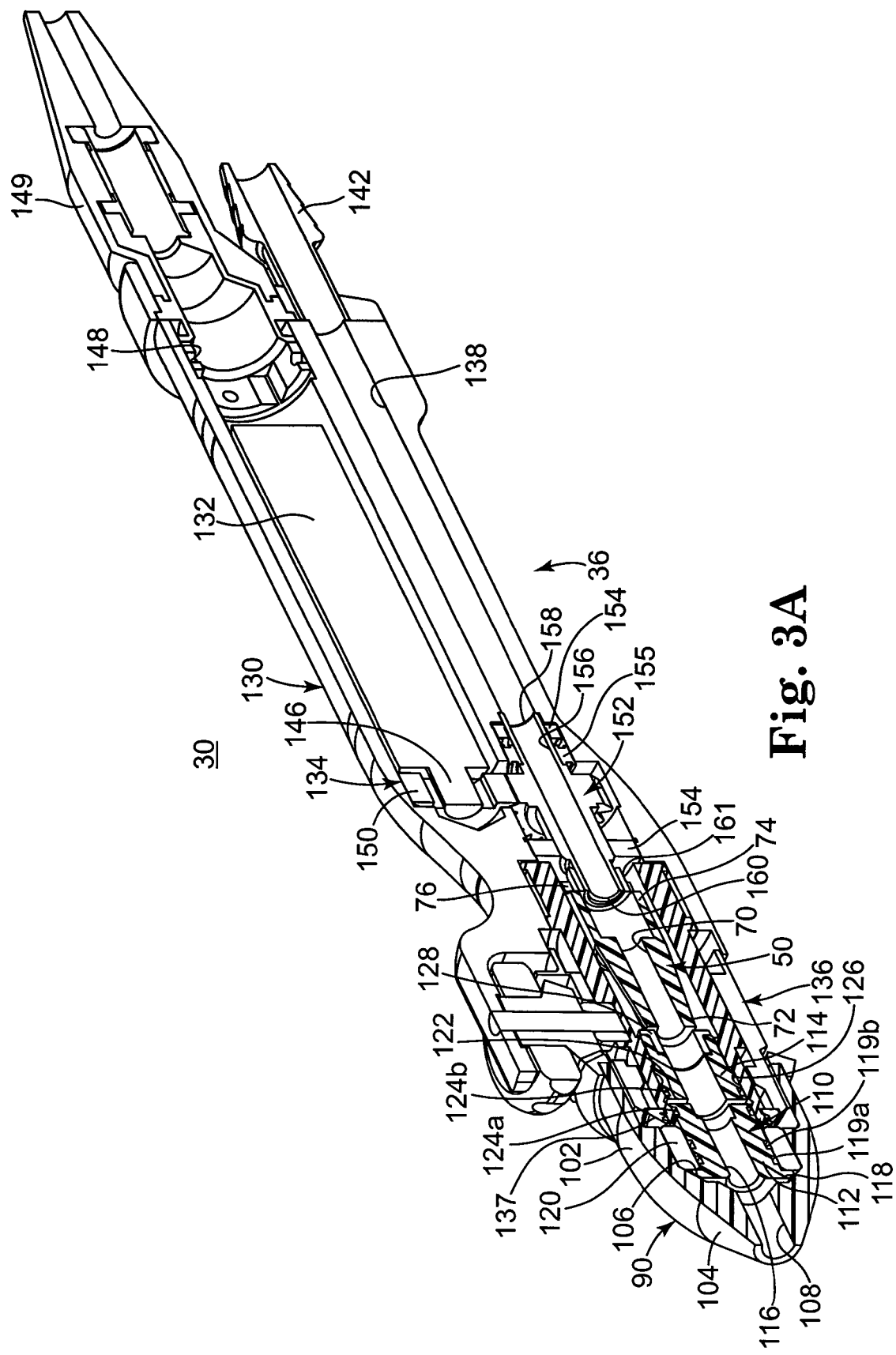
FIG. 3A is a cross-section view of a portion of the instrument of FIG. 2.

The second blade assembly 34 includes the second tubular member 44 forming the cutting window 46, and a second hub 90 (best shown in FIG. 3A). The second tubular member 44 defines a proximal region 92, a distal region 94, and a lumen 96 extending therebetween. In one embodiment, the distal region 94 integrally forms the cutting window 46 that is otherwise fluidly connected to the lumen 96. Alternatively, a tip member that otherwise forms the cutting window 46 can be separately manufactured and assembled to the second tubular member 44. Regardless, the cutting window 46 is preferably defined by a serrated edge 98. In one embodiment, the second tubular member 44 is rigid and longitudinally straight or linear. In alternative embodiments described below, the second tubular member 44 can incorporate, or be forced to assume, one or more bends. Regardless, the second tubular member 44, and in particular the lumen 96, is sized to co-axially receive the first tubular member 40 in a manner that allows rotation and/or oscillation of the first tubular member 40 relative to second tubular member 44, as well as to provide a path for internal irrigation. To this end, and as described in greater detail below, the lumen 96 of the second tubular member 44 preferably has a diameter slightly greater than an outer diameter of a corresponding portion of the first tubular member 40, and defines an irrigation inlet 100 (referenced generally in FIG. 2) fluidly connected to the lumen 96.

As best shown in FIG. 3A, the second hub 90 includes a proximal zone 102 and a distal zone 104. The proximal zone 102 defines an inner surface 106 adapted to couple the second hub 90 to the handpiece 36 as described in greater detail below. The distal zone 104 forms a passage 108 sized to receive the proximal region 92 (FIG. 2) of the second tubular member 44 (FIG. 2) such that the second tubular member 44 rotates with rotation of the second hub 90.

In one embodiment, the second blade assembly 34 further includes an irrigation hub 110. The irrigation hub 110 is positioned within the proximal zone 102 of the second hub 90, and is defined by a distal segment 112 and a proximal segment 114 that combine to form a bore 116. The bore 116 has a diameter along the distal segment 112 commensurate with an outer diameter of the second tubular member 44 (FIG. 2) for fluidly connection with the lumen 96 of the second tubular member 44. Further, the bore 116 is sized to co-axially receive the first tubular member 40 such that the first tubular member 40 can freely rotate relative to the irrigation hub 110. The distal segment 112 terminates, in one embodiment, in a flange 118 adapted to mate against a corresponding surface of the second hub 90, and further forms circumferential slots 119a, 119b, each sized to receive a sealing member (not shown), such as an O-ring. As described in greater detail below, an outer surface of the distal segment 112 is further adapted to receive a mounting ring 120. The bore 116 has an enlarged diameter along the proximal segment 114 and is fluidly connected to an exterior of the irrigation hub 110 by a radial slot 122. In this regard, the proximal segment 114 forms circumferential grooves 124a, 124b at opposite sides of the radial slot 122, and a plurality of apertures or detents 126. The circumferential grooves 124a, 124b are each sized to receive a sealing member (not shown) such as an O-ring. The apertures 126 are each sized to receive a ball (not shown) as described below. Finally, in one embodiment, a bearing ring 128 is assembled to the proximal segment 114. For certain applications (such as where the surgical instrument 30 is adapted for performing a burring procedure), the bearing ring 128 can provide a wear-resistant bearing surface against which the first hub 50 rotates.

The second blade assembly 34 is assembled by mounting the second hub 90 over the irrigation hub 110. In one embodiment, the mounting ring 120 is employed to establish a desired interface between the hubs 90, 110, whereby the second hub 90 can rotate relative to the irrigation hub 110. For example, the mounting ring 120 is adhered to the outer hub 90 and positioned over the irrigation hub 110. In particular, the mounting ring 120 abuts the distal segment 112 of the irrigation hub 110, nesting against a proximal side (unnumbered) of the flange 118. A distal side of the flange 118, in turn, nests against the inner surface 106 of the second hub 90. The flange 118 is effectively loosely captured between the mounting ring 120 and the inner surface 106, thus rotatably securing the hubs 90, 110 to one another. The second tubular member 44 is mounted to the second hub 90, with the irrigation inlet 100 positioned proximal the irrigation hub 110. This arrangement establishes a fluid connection between the bore 116 of the irrigation hub 110, and in particular the radial slot 122, and the lumen 96 of the second tubular member 44. Regardless, the second tubular member 44 rotates with rotation of the second hub 90.

B. Handpiece 36

With continued reference to FIG. 3A, in one embodiment, the handpiece 36 includes a housing 130, a motor 132 (shown schematically in FIG. 3A), a drive coupling 134 (referenced generally in FIG. 3A), a sleeve 136, and a capture ring 137. As described in greater detail below, the housing 130 maintains the motor 132 and the drive coupling 134. The sleeve 136 and the capture ring 137 secure the hubs 50, 90 and the actuator assembly 38 to the handpiece 36.

Figure 3B:
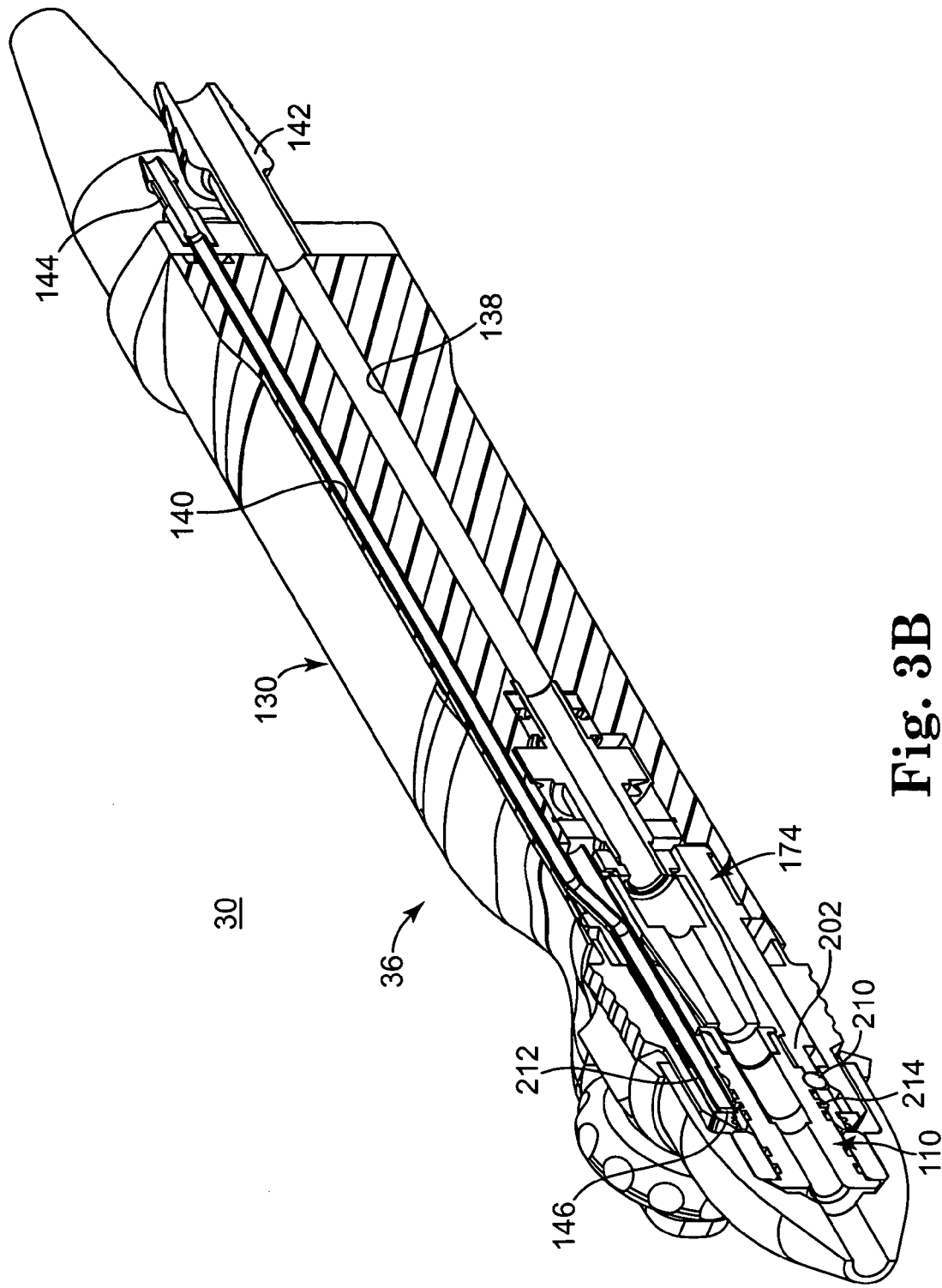
FIG. 3B is a cross-sectional view of a portion of the instrument of FIG. 2 illustrating an irrigation path.

The housing 130 can assume a variety of forms, but preferably defines an aspiration passageway 138 and an irrigation pathway 140 (shown in FIG. 3B). The aspiration passageway 138 is fluidly connected to a portion of the drive coupling 134 (as described below) that in turn is fluidly connected to the central passage 70 of the first hub 50. Thus, the aspiration passageway 138 is fluidly connected to the first tubular member 40 (FIG. 2) for aspirating material from the cutting tip 42. In this regard, and in one embodiment, the handpiece 36 further includes an aspiration port 142 assembled to the housing 130 in fluid communication with the aspiration passageway 138. Alternatively, the aspiration port 142 can be integrally formed by the housing 130. Regardless, the aspiration port 142 is adapted for connection to tubing (not shown) that in turn is connected to a vacuum source (not shown) for applying a vacuum to the aspiration passageway 138, and thus, the first tubular member 40. Alternatively, where the surgical cutting instrument 30 is adapted such that internal aspiration via the first tubular member 40 is not required (such as where the first tubular member 40 is not a tube), the aspiration passageway 138 can be eliminated.

With specific reference to FIG. 3B (where, for ease of illustration, only the housing 130 is shown with cross-hatching), the irrigation passageway 140 is formed within the housing 130, extending from an irrigation port 144 to an opening 146 adjacent the irrigation hub 110. The irrigation port 144, in turn, is adapted for fluid connection to tubing (not shown) that is otherwise connected to a fluid source (not shown). Thus, the handpiece 36 provides for internal irrigation. In one embodiment, the irrigation passageway 140 is defined by a tube extending within the housing 130. Alternatively, the housing 130 can form a bore that defines the irrigation passageway 140 without a separate tube. Conversely, and as described in greater detail below, the surgical cutting instrument of the present invention can be adapted to employ external irrigation.

Returning to FIG. 3A, the motor 132 is of a type known in the art and is enclosed within the housing 130. For ease of illustration, the motor 132 is shown schematically in the figures, and includes a drive shaft 146. In one embodiment, the housing 130 forms a conduit 148 and related port 149 through which wiring (not shown) can be maintained for electrically connecting the motor 132 to a power source (not shown). Alternatively, the surgical cutting instrument 30 can be configured such that the motor 132 is provided external the housing 130. Regardless, the drive shaft 146 is rotatably driven by the motor 132 and is connected to the drive coupling 134 as described below.

The drive coupling 134 includes a coupling ring 150, an output shaft 152, dynamic seals 154, and ball bearing assemblies 155 (one of which is schematically illustrated in FIG. 3A). The coupling ring 150 is secured to the drive shaft 136 and provides a toothed exterior surface (not shown). The output shaft 152 forms a corresponding toothed surface for interacting with the coupling ring 150, and is rotatably maintained relative to the housing 130 via the ball bearing assemblies 155. For ease of explanation, only the ball bearing assembly 155 proximal the coupling ring 150/output shaft 152 interface is shown in FIG. 3A, it being understood that a second ball bearing assembly (not shown) mounts the output shaft 152 to the housing 130 distal the coupling ring 150/output shaft 152 interface. With this configuration, rotation of the drive shaft 146 is transferred to the output shaft 152 via the coupling ring 150 to effectuate rotation of the first tubular member 40 via the first hub 50.

With the embodiment of FIG. 3A, the output shaft 152 defines a central passage 156 extending from a proximal end 158 to a distal end 160. The proximal end 158 is adapted to sealingly mate against the housing 130 in a region of the aspiration passageway 138 such that the central passage 156 of the output shaft 152 is fluidly connected to the aspiration passageway 138. Conversely, the distal end 160 is adapted for mounting to the proximal portion 72 of the first hub 50. In particular, the output shaft 152 is rigidly connected to the first hub 50 such that rotation of the output shaft 152 imparts a rotational motion onto the first hub 50. For example, the output shaft 152 can form, or have assembled thereto, an attachment feature 161 adapted to engage with the splines 76 of the first hub 50. Finally, the central passageway 156 is fluidly connected to the central passage 70 of the first hub 50 such that a fluid pathway is established between the cutting tip 42 (FIG. 2) of the first tubular member 40 and the aspiration port 142. The dynamic seals 154 fluidly seal the central passage 156 of the output shaft 152 relative to the aspiration passageway 138 and the central passage 70 of the first hub 50.

Figure 3C:
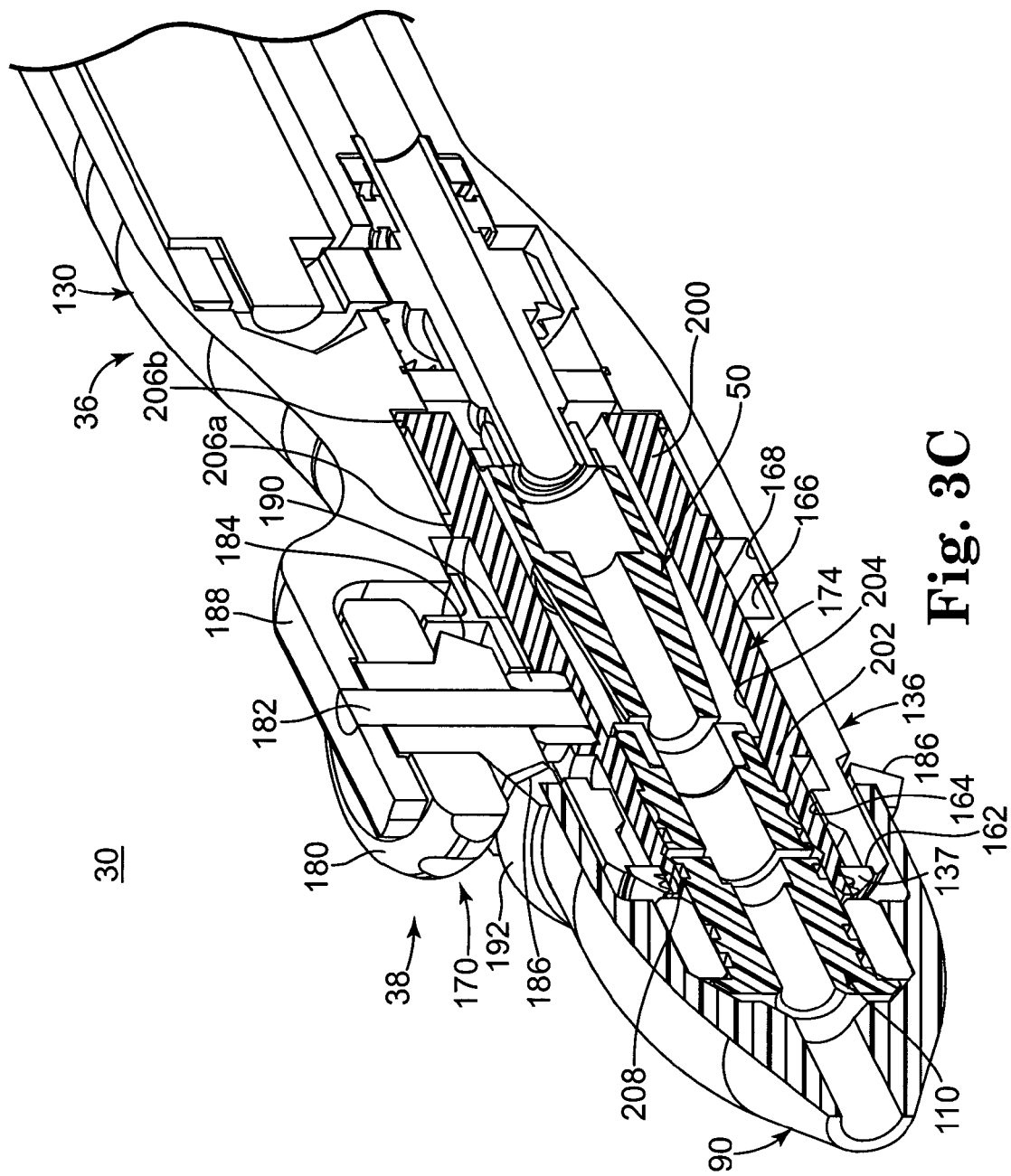
FIG. 3C is an enlarged cross-sectional view of a portion of the instrument of FIG. 3A.

The sleeve 136 supports and maintains the actuator assembly 38 and the irrigation hub 110 relative to the housing 130. In one embodiment and as best shown in FIG. 3C (where, for ease of illustration, not all components are shown with cross-hatching), the sleeve 136 forms a distal shoulder 152, an internal engagement face 164, and a proximal flange 166. The distal shoulder 162 is adapted to receive the capture ring 137. The internal engagement face 164 is adapted to receive and support a component of the actuator assembly 38 as described below. The proximal flange 166 is configured to nest against a projection 168 formed by the housing 130. Alternatively, the sleeve 136 can assume a variety of other forms and/or the housing 130 can be assembled to the various components with a number of differing techniques.

C. Actuator Assembly 38

With continued reference to FIG. 3C, the actuator assembly 38 is adapted to facilitate normal operation of the surgical cutting instrument, as well as to provide more convenient rotation of the second tubular member 44 (FIG. 2), and in particular the cutting window 46 (FIG. 2), relative to the handpiece 36. With this in mind, the actuator assembly 38 includes an actuator mechanism 170 (referenced generally) and a collet 174. With the one embodiment of FIG. 3C, operation of the actuator mechanism 170 causes the second hub 90 to rotate relative to the collet 174 and thus relative to the handpiece 36.

In one embodiment, the actuator mechanism 170 includes an actuator 180, a shaft 182, a first set of gear teeth 184, and a second set of gear teeth 186. With the one embodiment of FIG. 3C, the actuator 180 is a wheel mounted to the shaft 182 and the first set of gear teeth 184. In one embodiment, the wheel 180, the shaft 182, and the first set of gear teeth 184 are provided as separate components; alternatively, an integral structure can be provided. Regardless, the shaft 182 extends axially from the wheel 180, with the first set of gear teeth 184 being formed opposite the thumb wheel 180. Further, the shaft 182 rotatably connects the wheel 180 and the first set of gear teeth 184 relative to the housing 130, such as via an arm 188 formed by the housing 130 and a bushing 190 maintained within the housing 130. Regardless, the first set of gear teeth 184 rotate with rotation of the actuator 180 about an axis defined by the shaft 182. The first set of gear teeth 184 meshingly engage the second set of gear teeth 186. In one embodiment, the second set of gear teeth 186 are formed by a ring 192 that is otherwise mounted to the second hub 90. Alternatively, the second hub 90 can be configured to homogonously or integrally form the second set of gear teeth 186. Regardless, the first and second set of gear teeth 184, 186 form bevel or miter gears. With this construction, then, rotation of the wheel actuator 180 is translated to the second set of gear teeth 186 via the first set of gear teeth 184, thereby causing the second hub 90 to rotate.

The collet 174 is adapted to capture the irrigation hub 110, and thus various components connected thereto, to the housing 130 and includes a proximal region 200 and a distal region 202 that combine to form a passage 204 extending the length of the collet 174. A diameter of the passage 204 along the proximal region 200 is sized to co-axially receive the first hub 50 in a manner that allows the first hub 50 to freely rotate relative to the collet 174. In one embodiment, spaced apart, circumferential ribs 206a, 206b are formed at an exterior of the proximal region 200 for supporting the collet 174 relative to the housing 130. To this end, the collet 174 is preferably configured such that the proximal region 200 has a radially outward bias upon final assembly such that the ribs 206a, 206b serve to lock the collet 174 relative to the housing 130. More particularly, a tolerance ring (not shown) is positioned between the ribs 206a, 206b; when pressed together, the tolerance ring effectively press fits the collet 174 to the housing 130. Alternatively, a variety of other collet configurations can be employed for securing the collet 174 to the housing 130.

The passage 204 along the distal region 202 is sized for assembling the collet 174 over the irrigation hub 110. In one embodiment, the distal region 202 forms threads 208 for receiving the capturing ring 137, with the capture ring 137 forming corresponding threads. With this one configuration, then, assembly of the sleeve 136 to the collet 174 facilitates securement of the irrigation hub 110 to the collet 174. Further, in one embodiment, the collet 174 maintains a plurality of balls 210 (one of which is shown in FIG. 3B). The balls 210 are sized and positioned to selectively lock within a corresponding one of the apertures 126 (FIG. 3A) of the irrigation hub 110, thereby locking the irrigation hub 110 to the collet 174. To this end, the internal engagement face 164 of the sleeve 136 forces the balls 210 into engagement with the corresponding apertures 126. Alternatively, the collet 174 can be adapted to facilitate other assembly techniques.

As best shown in FIG. 3B, in one embodiment, the collet 174 further forms an internal slot 212 terminating in an aperture 214 at the distal region 202. The internal slot 212 is sized to receive the tube 140 or is otherwise fluidly connected to the irrigation port 144 (FIG. 3A). Regardless, the aperture 214 is fluidly connected to the radial slot 122 (FIG. 3A) of the irrigation hub 110 to fluidly connect the irrigation port 144 to the lumen 116 of the irrigation hub 110.

D. Surgical Cutting Instrument 30 Assembly

FIGS. 2-3C illustrate assembly of the handpiece 36, the actuator assembly 38, the first blade assembly 32, and the second blade assembly 34. The output shaft 152 is rotatably mounted within the housing 130 via the ball bearings 155 and is connected to the drive shaft 146 of the motor 132 via the coupling ring 150. The central passage 158 of the output shaft 152 is fluidly connected to the aspiration passageway 138 of the housing 130, with the dynamic seals 154 preferably effectuating a seal between the coupling hub 152 and the aspiration passageway 158.

The actuator mechanism 170 is assembled to the housing 130 as shown, except for the second set of gear teeth 186 that are, in one embodiment, otherwise provided with the second hub 90. Thus, assembly of the second set of gear teeth 186 to the first set of gear teeth 184 are described in greater detail below. The collet 174 is assembled to the housing 130, with the tolerance ring (not shown) achieving a press fit between the components. The sleeve 136 is co-axially positioned over the collet 174. A spring (not shown) is positioned over the collet 174, residing in a gap defined between the projection 168 of the housing 130 and the proximal flange 166 of the sleeve 136. The spring serves to bias the collet 174 axially away from the housing 130. Conversely, the capture ring 137 is threaded onto the threads 208 of the collet 174 and nests against the distal shoulder 162 of the sleeve 136. Rotation of the capture ring 137 over the collet 174 forces the sleeve 136 axially towards the housing 130 via interface with the distal shoulder 162, overcoming a bias of the spring otherwise positioned between the housing projection 168 and the proximal flange 166 of the sleeve 136. Thus, the capture ring 137 and the spring serve to lock the sleeve 136 relative to the housing. Upon final assembly, the collet 174 is rotationally positioned to receive (or otherwise be fluidly connected to) the irrigation passageway 140.

The first blade assembly 32 includes the first tubular member 40 assembled to the first hub 50 at the proximal portion thereof. With specific reference to FIG. 3A (in which the first tubular member 40 is not shown for purposes of clarification), the first blade assembly 32 is assembled to the handpiece 36 by mounting the first hub 90 to the output shaft 152. In one embodiment, the splines 76 of the first hub 90 mesh with the engagement feature 161 of the output shaft 152, with a friction fit being achieved between the two components. Further, the first tubular member (FIG. 2) extends within the central passage 156 of the output shaft 152, with a gasket (not shown) disposed within the passage 70 of the first hub 50 to effectuate a seal. Alternatively, other assembly techniques can be employed to fluidly connect the lumen 56 of the first tubular member 40 with the aspiration port 152. Regardless, assembly of the first blade assembly 32 is such that the first tubular member 40 rotates with rotation of the output shaft 152 via the first hub 50.

The second blade assembly 34 includes the second tubular member 44, second hub 90, and the irrigation hub 110. With specific reference to FIGS. 3A and 3C (in which the second tubular member 44 is not shown for purposes of clarification) the second blade assembly 34 is assembled to the handpiece 36 by simultaneous mounting of the second hub 90 and the irrigation hub 110. The second hub 90 is loosely connected to the irrigation hub 110 via the mounting ring 120 as previously described. The irrigation hub 110 is co-axially disposed over the first tubular member 40 (FIG. 2) and locked onto the collet 174. In this regard, the sleeve 136 is first retracted proximally to release the balls 210 (FIG. 3B), thus allowing the irrigation hub 110 to slide within the collet 174. The irrigation hub 110 is positioned such that the apertures 126 are aligned with respective ones of the balls 210 otherwise maintained by the collet 174. The sleeve 136 is then released, such that the internal engagement face 164 forces the balls 210 into the apertures 126, thereby locking the irrigation hub 110 to the collet 174. Regardless, the radial slot 122 of the irrigation hub 110 is fluidly connected to the lumen 116 of the irrigation hub 110. O-rings (not shown) are disposed within the grooves 124a, 124b to effectuate a complete seal.

The second hub 90 (to which the second tubular member 44 (FIG. 2) is attached) is similarly co-axially received over the first tubular member 40 (FIG. 2). Upon final assembly of the irrigation hub 110 to the collet 174, the second set of gear teeth 186 (otherwise mounted to the second hub 90) mesh with the first set of gear teeth 184. With additional reference to FIG. 2, the inlet 100 of the second tubular member 44 is fluidly connected to the lumen 116 of the irrigation hub 110, and thus to the irrigation port 144 (FIG. 3B). O-rings (not shown) are disposed in the circumferential slots 119a, 119b to ensure that fluid flows from the irrigation port 144 to the lumen 56 of the second tubular member 44 and not outwardly between the second hub 90 and an exterior of the irrigation hub 110. Regardless, the second hub 90 can rotate relative to the irrigation hub 110.

Where the blade assemblies 32, 34 are adapted to performing a cutting operation (e.g., the cutting tip 42 has serrated edges and the cutting window 46 has serrated edges), the cutting tip 42 nests against an interior, distal end of the second tubular member 44, such that a slight gap is generated between the first hub 50 and the irrigation hub 110 as best shown in FIG. 3C. Alternatively, for other blade configurations/uses, such as with a burring application in which the cutting tip 42 forms a bur, the irrigation hub 110 contacts the first hub 90 to establish a desired location of the cutting tip 42 relative to the cutting window 46, with the bearing ring 128 providing a low wear surface against which the first hub 50 contacts and rotates.

E. General Operation

Figure 4A:
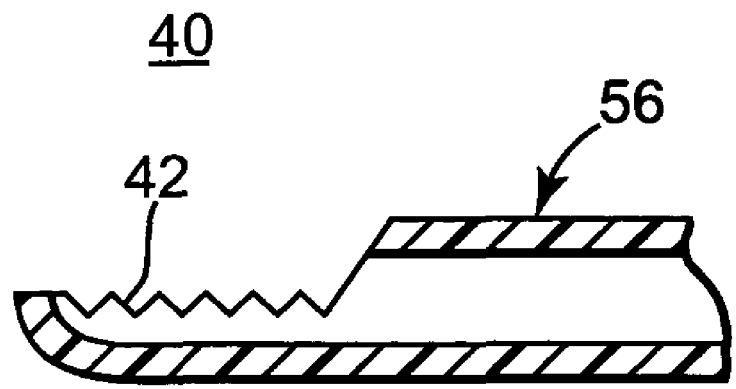
FIG. 4A is an enlarged, cross-sectional view of a portion of an inner tubular member of the instrument of FIG. 1.
Figure 4B:
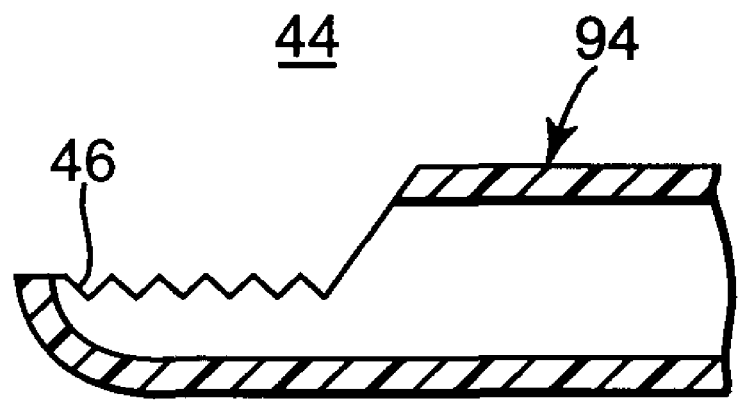
FIG. 4B is an enlarged, cross-sectional view of a portion of an outer tubular member of the instrument of FIG. 1.

Upon final assembly, the cutting tip 42 provided by the first tubular member 40 is selectively exposed at the cutting window 46. To this end, FIG. 4A provides an enlarged, cross-sectional view of the distal portion 56 of the first tubular member 40, including the cutting tip 42, whereas FIG. 4B illustrates the distal region 94 of the second tubular member 44, including the cutting window 46. Upon final assembly, and as best shown in FIG. 2, the cutting tip 42 is positioned at the cutting window 46 with the two components being rotatable relative to one another. By way of explanation, FIG. 2 illustrates the first tubular member 40 rotated to a position whereby the cutting tip 42 is exposed via the cutting window 46. Upon rotation of the first tubular member 40 relative to the second tubular member 44, or vice-versa, an opposite side of the first tubular member 40 will be positioned at the cutting window 46, such that the central lumen 56 of the first tubular member 40 is closed relative to the cutting window 46. Regardless, the cutting tip 42 and the cutting window 46 combine to define a cutting implement 230.

Figure 5A:
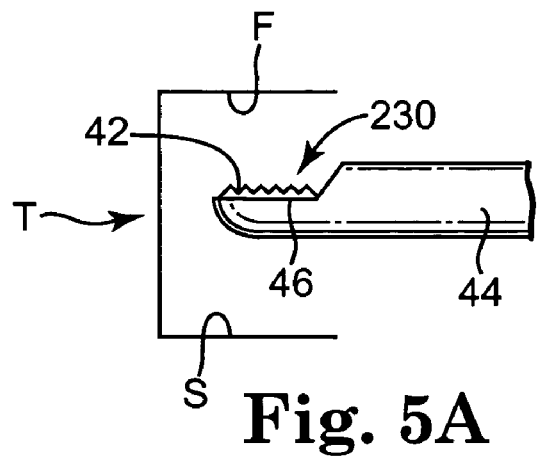
FIGS. 5A-5C are simplified, side views of a portion of the instrument of FIG. 1 deployed at a target site illustrating use of the instrument.

Specific surgical techniques facilitated by the surgical cutting instruments are described below in connection with an alternative embodiment design. In general terms, however, during use, a hand (not shown) of a user (not shown) is employed to grasp the handpiece 36, and in particular the housing 130. In this regard, and in one embodiment, the housing 130 forms an exterior contour adapted to ergonomically fit within a user's hand, such as by grasping the housing 130 adjacent the arm 188 (FIG. 3C). Regardless, the user then deploys the cutting implement 230, manipulating the handpiece 36 to deploy the cutting implement 230 to a target site T as schematically shown in FIG. 5A. As a point of reference, the highly simplified target site T of FIG. 5A includes a first surface F and a second surface S. Further, for ease of illustration, the cutting window 46 associated with the second tubular member 44 is shown without the serrated edges (98 in FIG. 3A) to better show the cutting tip 42. With this in mind, and following initial deployment to the target site T of FIG. 5A, the cutting window 46 has a first spatial orientation relative to the target site T and the handpiece 36 (FIG. 1). More particularly, with the orientation of FIG. 5A, the cutting window 46 faces, or is open to, the first surface F of the target site T. Further, the handpiece 36, and in particular the housing 130, can be generally described as defining a first side 240 and a second side 242 as identified in FIG. 1. The sides 240, 242 conform with an orientation of the housing 130 when naturally grasped by the user's hand, with the first side 240 positioned within the user's palm, such that the wheel actuator 180 is proximate the user's thumb or index finger (not shown). By way of further example, the cutting implement 230 is deployed to the orientation of FIG. 5A with the first side 240 of the housing 120 being above the second side 242, with the cutting window 46 "facing" or being open relative to the first side 240 of the housing 130.

With the above conventions in mind, then, the surgical cutting instrument 30 can then be operated to remove tissue from the first surface F of the target site T. The surgical procedure in question may then require removal of tissue from the second surface S (or removal of tissue from the second surface S only). In the orientation of FIG. 5A, the cutting window 46 is away from the second surface S, requiring movement of the cutting window 46 to allow the cutting tip 42 to interact with the second surface S. To accomplish alteration of the spatial orientation of the cutting window 46, and with additional reference to FIG. 3A, the user (not shown) rotates the wheel actuator 180 in a desired direction. In particular, the user's thumb (not shown) and/or index finger (not shown) of the hand that is otherwise grasping the housing 130 is used to rotate the wheel actuator 180. Rotation of the wheel actuator 180 is translated to the second hub 90 via the gear teeth 184, 186. Rotation of the second hub 90, in turn, causes the second tubular member 44, and thus the cutting window 46, to rotate relative to the target site T and the handpiece 36. Rotation of the wheel 180 continues until the cutting window 46 assumes the second spatial orientation shown in FIG. 5B. Notably, a rotational orientation of the handpiece 36, and in particular the housing 130, need not change when translating the cutting window 46 from the spatial orientation of FIG. 5A to the spatial orientation of FIG. 5B. That is to say, in the position of FIG. 5B, the cutting window 46 faces or is open to not only the second surface S, but also the second side 242 of the housing 130.

Figure 5B:
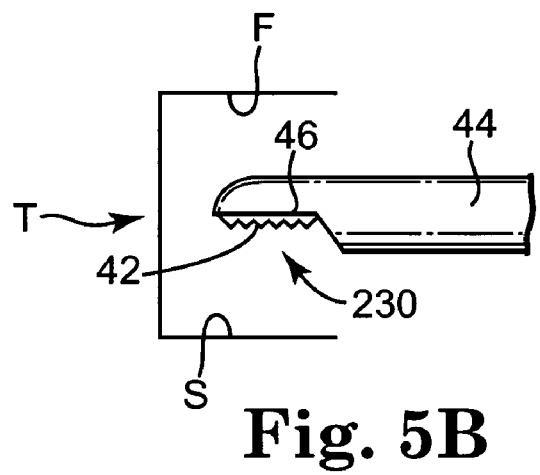

Transition of the cutting window 46 from the spatial orientation of FIG. 5A to the spatial orientation of FIG. 5B is accomplished, in one embodiment, with only a single hand of the user. The surgical cutting instrument 30 is configured such that the cutting window 46 can be spatially rotated relative to the handpiece 36 without requiring both hands of the user to otherwise grasp the handpiece at two discrete locations and apply a twisting or torque-generating motion. In one embodiment, the single-handed cutting window rotation is accomplished by configuring the actuator assembly 38 such that a movement axis of the wheel actuator 180 is off-set from an axis of the second hub 90. That is to say, the wheel actuator 180 moves (e.g. rotates) about an axis or plane that is not co-axial with an axis of the second hub 90; instead, movement of the wheel actuator 180 is translated into rotation of the second hub 90 about the axis of the second hub 90. With this approach, then, and unlike previous designs, the thumb wheel actuator 180 can be located at any desired position relative to the housing 130 so as to promote single-handed operation.

Figure 5C:
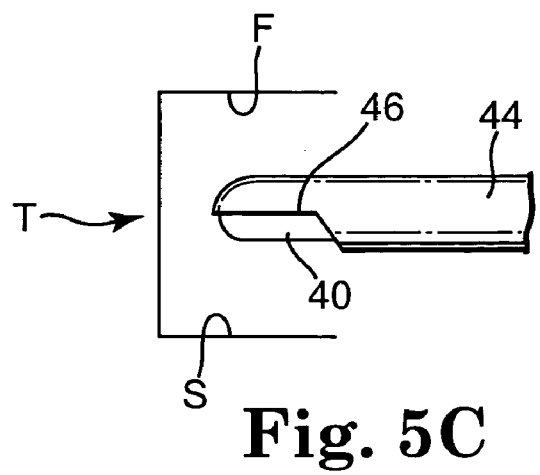

Notably, while the cutting tip 42 is illustrated in FIG. 5B as being exposed via the cutting window 46, the surgical cutting instrument 30 of the present invention can further be operated to readily "close" the cutting tip 42 relative to the second tubular member 44. In particular, FIG. 5C illustrates a transition from the arrangement of FIG. 5A whereby the first tubular member 40, and thus the cutting tip 42 (FIG. 5A), remains stationary with rotation of the second tubular member 44, and thus the cutting window 46, in the manner previously described. The cutting tip 42 is thus "closed" relative to the cutting window 46, such that tissue or other material is prevented from entering the lumen 56 (FIG. 2) of the first tubular member 40.

Figure 6A:
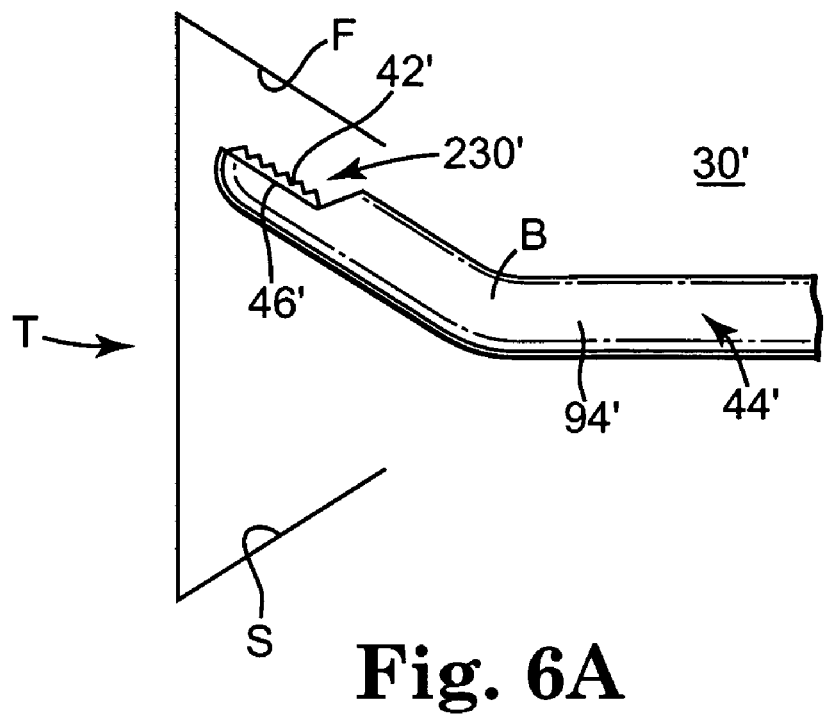
FIGS. 6A and 6B are simplified, side views of an alternative embodiment instrument deployed at a target site illustrating use of the instrument.
Figure 6B:
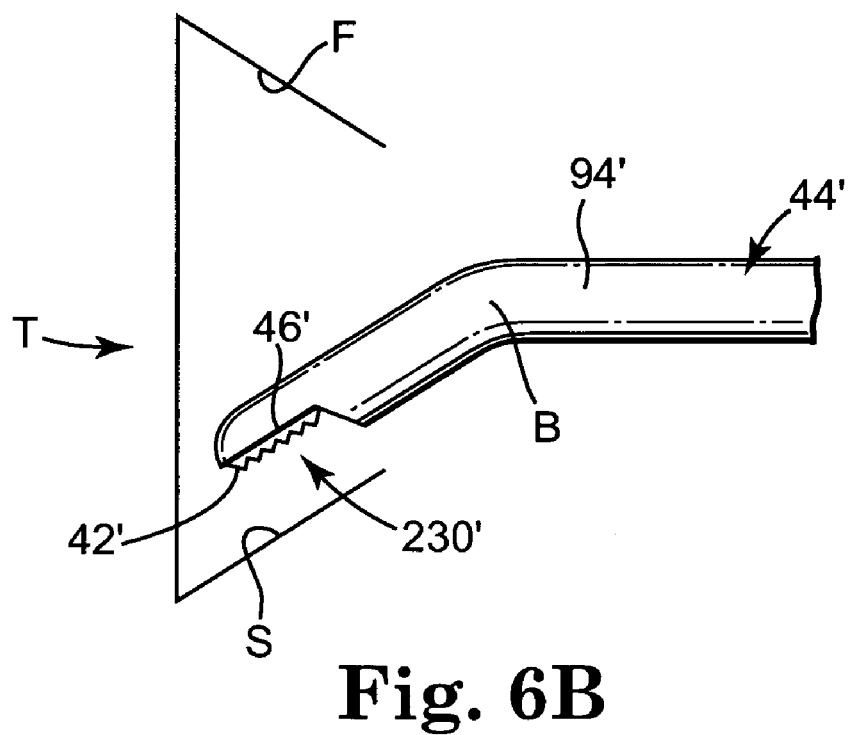

While the surgical cutting instrument 30 has been described as employing straight or linear tubular members 40, 44, alternative constructions are equally acceptable. For example, the first and second tubular members 40, 44 can be adapted to provide one or more bends or curves. With this in mind, the bent or curved tubular members 40, 44 are assembled to the handpiece 36 in a manner identical to that previously described. During use, and as shown in FIG. 6A, the resultant cutting implement 230' is deployed to a target site T otherwise having a first surface F and a second surface S. By way of reference, FIG. 6A depicts a distal portion of the alternative cutting instrument 30' otherwise including a second tubular member 44' defining a bend and maintaining a first tubular member (not shown) having a cutting tip 42'. As with the previous embodiments, the cutting tip 42' is selectively exposed via a cutting window 46' (shown without serrated edges) formed by the second tubular member 44'. With these conventions in mind, following deployment, the cutting window 46' faces or is open relative to the first surface F in FIG. 6A. Where desired, the spatial orientation of the cutting window 46' can be altered by a user (not shown) using a single hand to manipulate the actuator wheel 180 (FIG. 3A). As previously described, rotation of the actuator wheel 180 is translated to the first hub 90 (FIG. 3A) that in turn causes the second tubular member 44' to rotate relative to the handpiece 36 (FIG. 2). Due to a preferred rigid construction of the second tubular member 44', rotation of the second hub 90 causes a distal region 94' of the second tubular member 44' to effectively spatially rotate about a bend point B, transitioning to the spatial orientation of FIG. 6B. Rotation of the thumb wheel 180 is continued until the cutting window 46 faces or is opened to the second surface S for subsequent operation of the cutting tip 42'. Once again, however, a rotational orientation of the handpiece 36 (FIG. 1) need not change to accomplish desired spatial re-positioning of the cutting window 46' and only one hand of the user is necessary.

With specific reference to FIGS. 2 and 3A, while the surgical cutting instrument 30 has been described as including two of the tubular members 40, 44, in an alternative embodiment, and additional, third tubular member (not shown) can be included. With this alternative embodiment, the first and second tubular members 40, 44 are essentially identical to that previously described, with the second tubular member 44 forming the cutting window 46 within which the cutting tip 42 is disposed. However, with the three-tube embodiment, the second tubular member 44 extends through the hub 90 and is mounted to the irrigation hub 110. With this configuration in mind, the third tubular member is co-axially disposed over the second tubular member 44 and is attached to the second hub 90. Further, a distal end of the third tubular member terminates proximal the cutting window 46 of the second tubular member 44. By forming the third tubular member to form a rigid bend, this configuration can more readily achieve the bend shown in FIG. 6A. During use, the first tubular member 40 is rotated relative to the second tubular member 44 to effectuate tissue removal via the cutting tip 42 at the cutting window 46. A spatial, rotational position of the cutting window 46 can be changed by, for example, manipulating the wheel 180 (FIG. 3C) that in turn causes the third tubular member to rotate, effectively about its bend point. This, in turn, causes the cutting window 46 to, for example, transition from the spatial orientation of FIG. 6A to the spatial orientation of FIG. 6B.

F. Preferred, Alternative Surgical Cutting Instrument

Figure 7:
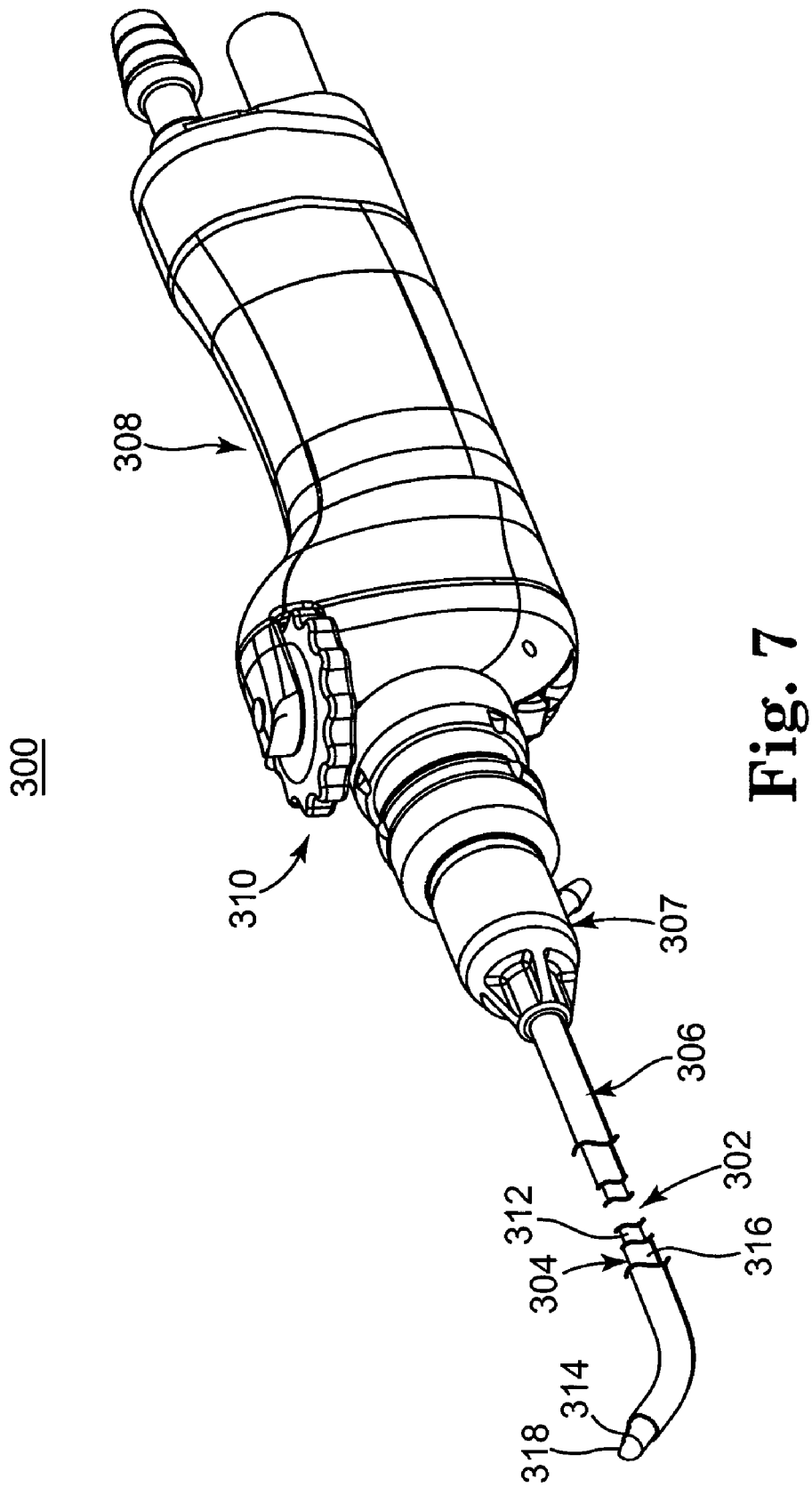
FIG. 7 is a perspective view of an alternative embodiment surgical cutting instrument in accordance with the present invention.

The surgical cutting instrument 30 described above can employ either a straight or bent tube configuration. Other alternative embodiments in accordance with the present invention can further facilitate implementation of a curved tube configuration. For example, FIG. 7 illustrates a preferred alternative surgical cutting instrument 300 including a first blade assembly 302 (referenced generally in FIG. 7), a second blade assembly 304 (referenced generally in FIG. 7), a support tube assembly 306, an irrigation assembly 307, a handpiece 308, and an actuator assembly 310 (referenced generally in FIG. 7). Details on the various components are described below. In general terms, however, the first blade assembly 302 includes a first tubular member 312 and a cutting tip 314 (referenced generally in FIG. 7). The second blade assembly 304 includes a second tubular member 316 forming a cutting window 318 (referenced generally in FIG. 7). The first tubular member 312 is co-axially disposed within the second tubular member 316 such that the cutting tip 314 is selectively exposed at the cutting window 318. The second tubular member 316 is co-axially disposed within the support tube assembly 306 that otherwise forms at least one bend. The irrigation assembly 307 connects a fluid source (not shown) to the second blade assembly 304. The support tube assembly 306, first tubular member 312, and second tubular member 316 are mounted to the handpiece 308. In this regard, the actuator assembly 310 is adapted to facilitate rotation of the cutting window 318 relative to the handpiece 308 while the support tube 306 remains stationary.

Figure 8A:
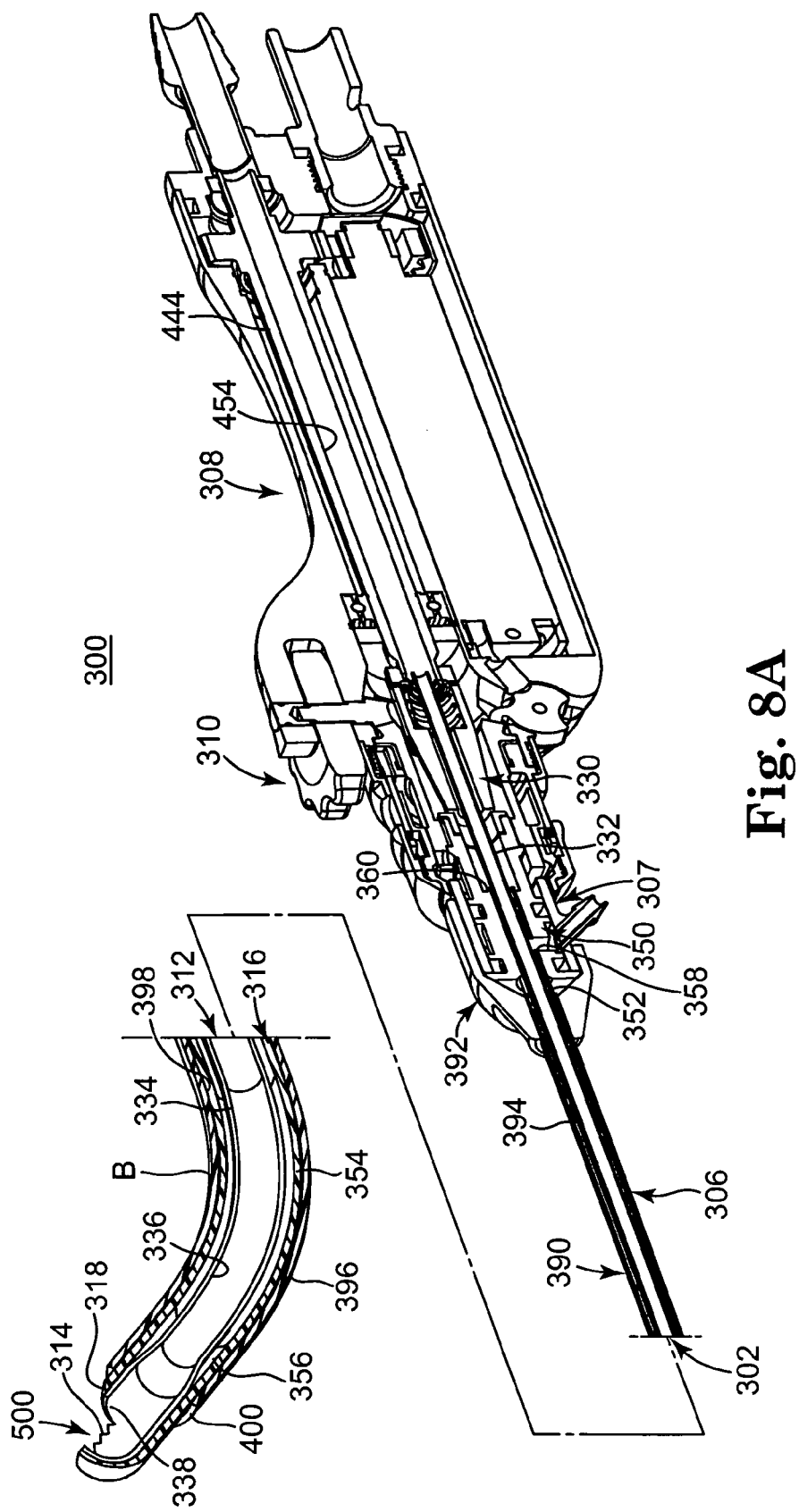
FIG. 8A is a partial, cross-sectional view of the instrument of FIG. 7 with portions enlarged.

The first blade assembly 302 is shown in greater detail in FIG. 8A and includes the first tubular member 312 forming the cutting tip 314, and a first hub 330. The first tubular member 312 defines a proximal section 332, a distal section 334, and a central lumen 336 extending therebetween. Once again, the cutting tip 314 can assume a variety of forms other than the serrated edge configuration depicted in FIG. 8A. For example, the cutting tip 314 can be a bur, and the first tubular member 312 need to not be a tube, but can instead be a solid shaft. In one embodiment, the first tubular member 312 defines a distal opening 338 fluidly connected to the lumen 336. Further, the tubular member 312 is configured to conform to a bend defined by the support tube assembly 306 (described below). For example, in one embodiment, the first tubular member 312 has dovetail cuts (not shown) along a portion of a longitudinal length thereof in a region of an expected bend (generally referenced by "B" in FIG. 8A). Alternatively, other configurations can be employed by which the first tubular member 312 will follow the bend B and allow high-speed rotation of the first tubular member 312 during a surgical procedure. Regardless, the proximal section 332 is mounted to the first hub 330 that is otherwise mounted to the handpiece 308. In one embodiment, the first hub 330 is highly similar to the first hub 50 (FIG. 3A) previously described, and defines a passage 338.

The second blade assembly 304 includes the second tubular member 316 forming the cutting window 318, and a second hub 350. The second tubular member 316 defines a proximal region 352, a distal region 354, a lumen 356, and a radial passage 358. The lumen 356 extends from the cutting window 318, otherwise formed at the distal region 354, to a proximal, open end 360. The radial passage 358 is formed in the proximal region 352 adjacent the proximal end 360, and fluidly connects the lumen 356 to an exterior of the second tubular member 316. In this regard, the lumen 356 defines a diameter slightly greater than an outer diameter of the first tubular member 312, such that the first tubular member 312 is co-axially received with the lumen 356, as well as provides sufficient spacing for flow of liquid between the first and second tubular members 312, 316. Similar to the first tubular member 312, the second tubular member 316 is configured to conform to the bend B defined by the support tube assembly 306, and as such can incorporate a series of dovetail cuts (not shown) along a portion of a longitudinal length thereof. In one embodiment, a coating (not shown) is applied over at least the distal region 354 of the second tubular member 316 to minimize undesired rotation or oscillation of the second tubular member 316 relative to the support tube assembly 306 upon rotation/oscillation of the first tubular member 312. The coating can assume a variety of forms, and preferably is polyester shrink tubing. Alternatively, the coating can be eliminated.

Figure 8B:
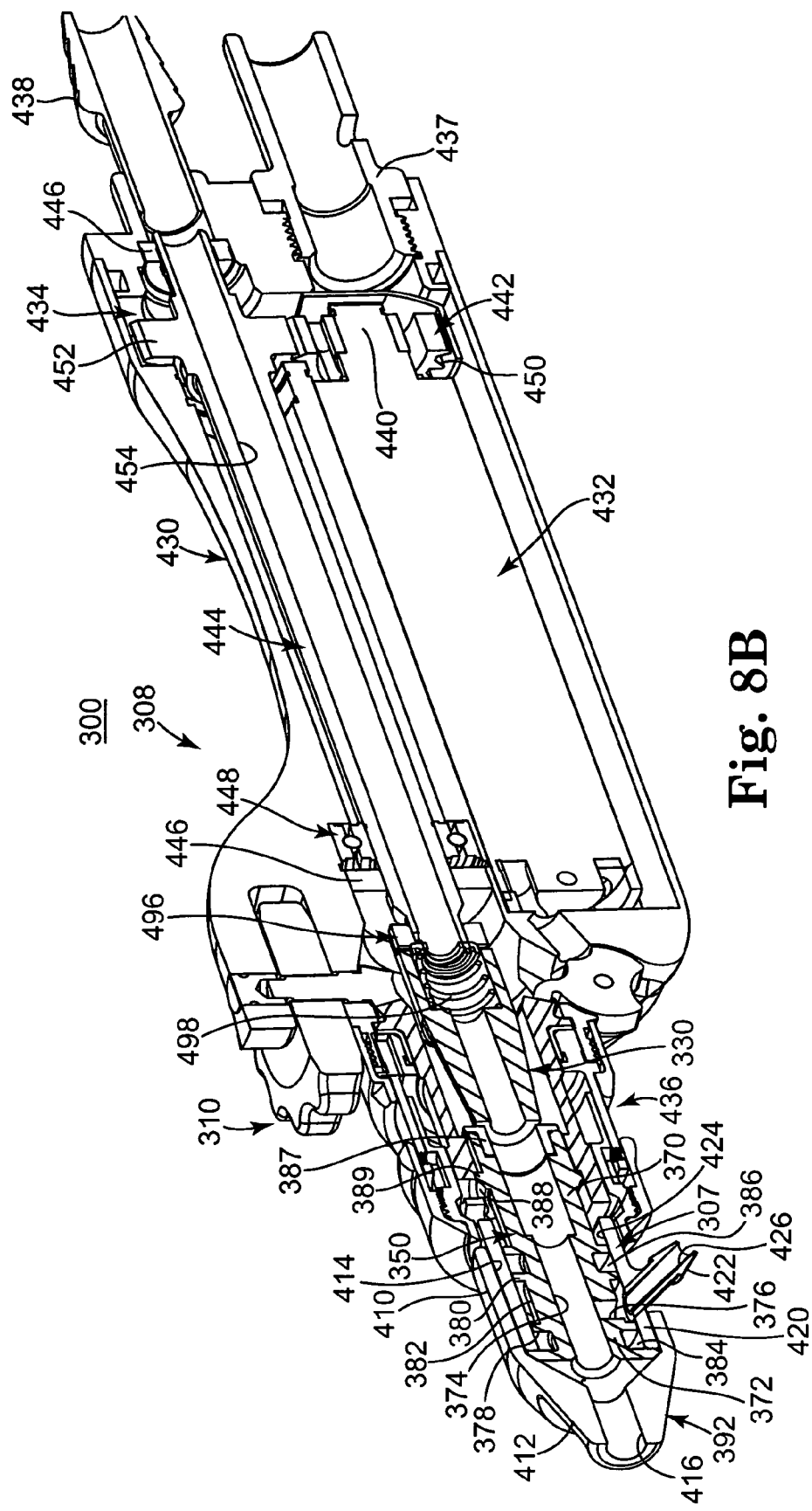
FIG. 8B is a partial, cross-sectional view of a portion of the instrument of FIG. 7.

The second hub 350 is mounted about the proximal region 352 of the second tubular member. With additional reference to FIG. 8B, that otherwise depicts the surgical cutting instrument 300 with the support tube 306, first tubular member 312, and the second tubular member 316 removed and illustrates only portions thereof with cross-hatching for ease of understanding, the second hub 350 is similar to the irrigation hub 110 (FIG. 3A) previously described and defines a proximal portion 370, a distal portion 372, a central passage 374, and an irrigation passageway 376. The central passage 374 extends from the proximal portion 370 to the distal portion 372. In one embodiment, the central passage 374 has an enlarged diameter at the proximal portion 370 as compared to the distal portion 372. Regardless, the central passage 374 at the distal portion 372 is sized for mounting over the proximal region 352 of the second tubular member 316. The irrigation passageway 376 fluidly connects the central passage 374 to an exterior of the second hub 350. In one embodiment, the distal portion 372 further includes opposing support flanges 378, 380, that define a circumferential groove 382. As described in greater detail below, the circumferential groove 382 is fluidly connected to the irrigation passageway 376 and provides a fluid pathway to the irrigation assembly 307. Slots 384, 386 are formed distal and proximal the groove 382 and are sized to receive O-rings (not shown) that otherwise seal the groove 382. In one embodiment, the proximal portion 370 is adapted for receiving a ring 387 that, for certain blade assembly configurations (e.g., a bur application) otherwise provides a low-wear bearing surface against which the first hub 330 rotates. Further, the proximal portion 370 forms a plurality of exterior detents 388 (one of which is shown in FIG. 8B) and a circumferential rib 389. As described in greater detail below, the detents 388 and the rib 389 facilitate assembly of the second hub 350 to with the actuator assembly 310.

With continued reference to FIGS. 8A and 8B, the support tube assembly 306 includes a third tubular member 390 and a third hub 392. The third tubular member 390 defines a proximal portion 394, a distal portion 396, and a lumen 398 extending therebetween. The lumen 398 is sized to co-axially receive the second tubular member 316. In one preferred embodiment, the third tubular member 390 is of a rigid construction and defines the bend B along a longitudinal length thereof. The flexible zones associated with the first and second tubular members 312, 316, as described above, allow the first and second tubular members 312, 316 to conform to the bend B upon final assembly, with the third tubular member 390 terminating at a distal end 400.

The proximal portion 394 of the third tubular member 390 is mounted to the third hub 392. In this regard, and with specific reference to FIG. 8B, the third hub 392 includes a proximal section 410 and a distal section 412. The proximal section 410 forms an aperture 414, whereas the distal section 412 defines a passage 416. The aperture 414 is sized for mounting to the actuator assembly 310 such that the second hub 350 is rotatable relative to the third hub 392. The passage 416, in turn, is sized in accordance with an outer diameter of the third tubular member 390 (FIG. 8A) such that the third tubular member 390 is affixed to the third hub 392.

The irrigation assembly 307 includes an irrigation hub 420 and an irrigation port 422. The irrigation hub 420 defines a passage 424 sized for mounting about the second hub 350 as described in greater detail below. The irrigation port 422 extends from the irrigation hub 420 and forms an irrigation pathway 426 fluidly connected to the passage 424 for delivering liquid to the second tubular member 316 as described below.

The handpiece 308 includes a housing 430, a motor 432 (shown schematically in FIG. 8B), a drive coupling 434, and a mounting assembly 436 (referenced generally). As with previous embodiments, the motor 432 is secured within the housing 430. In this regard, the housing 430 forms a conduit 437 through which wiring (not shown) otherwise providing power to the motor 432 can extend. Further, the housing 430 preferably forms an aspiration port 438 for fluidly connecting the passage 338 of the first hub 330 to a vacuum source (not shown), as described below.

In one embodiment, the drive coupling 434 mechanically connects a drive shaft 440 of the motor 432 to the first hub 330, and includes a drive ring 442, an output shaft 444, dynamic seals 446, and ball bearing assemblies 448 (one of which is shown in FIG. 8B). The drive ring 442 is mounted to the drive shaft 440 and forms a gear 450. Conversely, the output shaft 444 forms teeth 452 that mesh with the gear 450. The output shaft 444 is rotatably mounted within the housing 430 by the ball bearing assemblies 448. For ease of illustration, a ball bearing assembly otherwise mounting the output shaft 444 to the housing 430 proximal the teeth 452 is omitted from the views of FIGS. 8A and 8B. Regardless, the output shaft 444 forms a passage 454. Upon final assembly, the passage 454 fluidly connects the aspiration port 438 and the lumen 338 of the first hub 330, with the dynamic seals 446 ensuring a fluid-tight seal. Alternatively, other constructions can be employed.

Figure 8C:
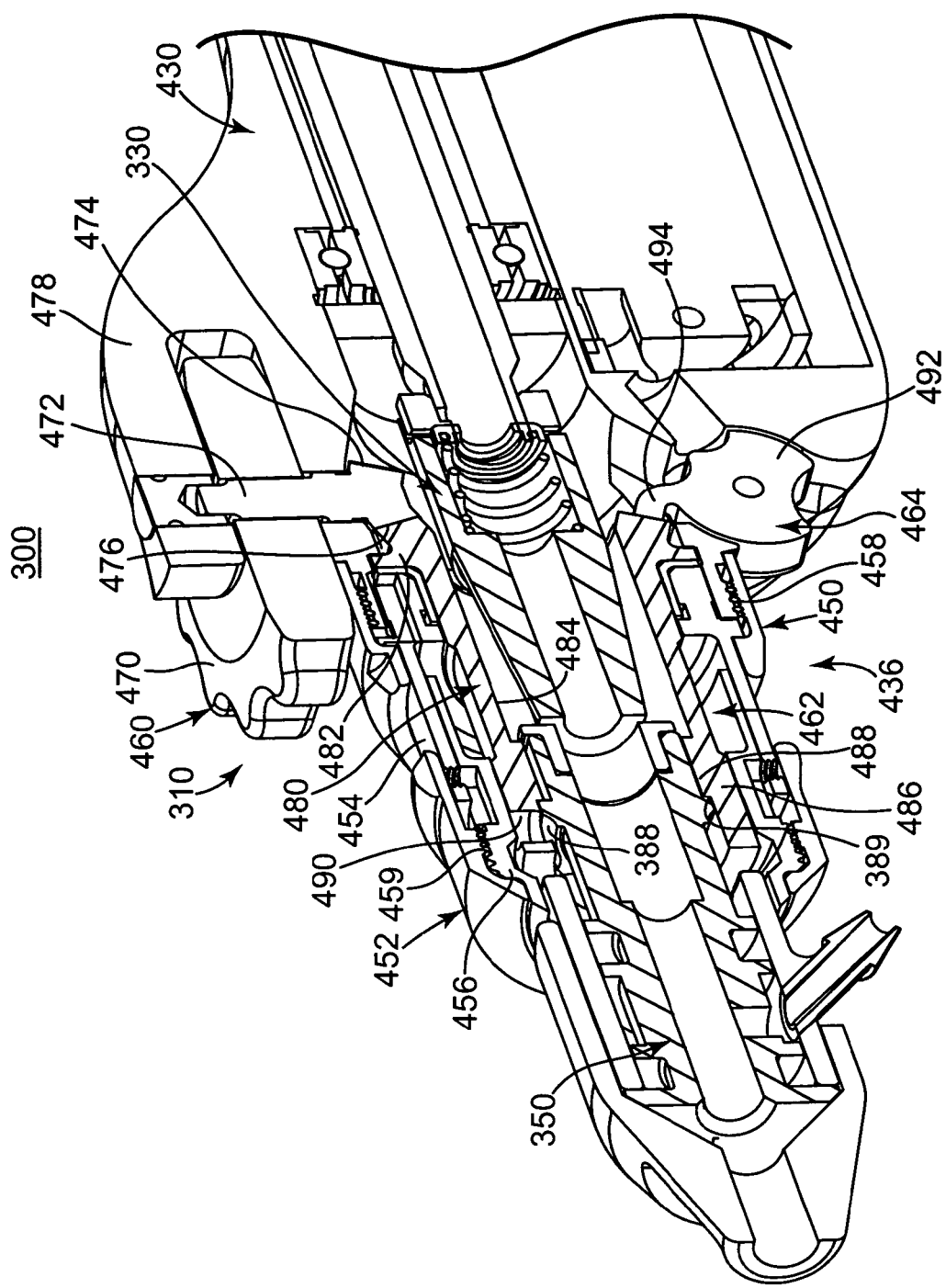
FIG. 8C is an enlarged, cross-sectional view of a portion of FIG. 8B.

As best shown in FIG. 8C (in which only portions are shown with cross-hatching for ease of illustration), in one embodiment, the mounting assembly 436 includes first and second capture rings 450, 452, first and second sleeves 454, 456. As described in greater detail below, the capture ring 450 defines an interior threaded surface 458 and is adapted to couple the sleeve 454 to a component of the actuator assembly 310. Similarly, the capture ring 452 defines an interior, threaded surface 459 and is adapted to couple the sleeve 456 to a component of the actuator assembly 310.

The actuator assembly 310 facilitates rotation of the second tubular member 316 as described below, and includes an actuator mechanism 460, a collet assembly 462, and a locking mechanism 464. The actuator mechanism 460 includes an actuator 470, a shaft 472, a first set of gear teeth 474, and a second set of gear teeth 476. The actuator 470 is preferably a wheel. The shaft 472 extends from a central axis of the wheel 470 and facilitates assembly of the wheel 470 to the housing 430, such as an arm 478 formed by the housing 430. The first set of gear teeth 474 are formed on or by the shaft 472 opposite the wheel 470. In one embodiment, the first set of gear teeth 474 define a bevel gear. The second set of gear teeth 476 meshingly engage the first set of gear teeth 474. With the one embodiment of FIG. 8C, the second set of gear teeth 476 are provided as part of a component of the collet assembly 462 as described in greater detail below. Alternatively, the second set of gear teeth 476 can be separately formed and assembled to the corresponding collet assembly 462 component.

The collet assembly 462 includes a collet 480 and ball bearings (not shown). The collet 480 is configured to capture the second hub 350 relative to the housing 430 and preferably integrally forms the second set of gear teeth 476 at a proximal end 482 thereof. The collet 480 further forms a channel 484 sized to be received over the first hub 330 in a manner that allows the first hub 330 to freely rotate relative to the collet

480. A distal section 486 of the collet 480 preferably forms an inner flange 488 and a plurality of holes 490 (one of which is shown in FIG. 8C). The inner flange 488 is sized to abut the rib 389 of the second hub 350. The holes 490 are sized to capture individual ones of the spherical bearings that are otherwise partially received within a corresponding one of the detents 388 of the second hub 350. Thus, the collet 480 is mounted to the second hub 350 via the bearings.

The locking mechanism 464 includes a base 492, a finger 494 and a biasing device (not shown). The base 492 is rotatably or pivotably mounted to the housing 430. The finger 494 extends from the base 492 and is adapted to selectively engage the second set of gear teeth 476 otherwise provided on the collet 480. The biasing device biases the base 492 to the rotational position of FIG. 8B in which the finger 492 is engaged with the second set of gear teeth 476, thus preventing rotation of the collet 480. As described below, where rotation of the collet 480 is desired, the base 492 is pivoted or rotated to displace the finger 494 away from the second set of gear teeth 476. Alternatively, the locking mechanism 464 can assume other forms or can be eliminated.

Assembly of the surgical cutting instrument 300 generally entails assembly of the actuator assembly 310 to the handpiece 308, followed by consecutive mounting of the first blade assembly 302, the second blade assembly 304, and the support tube assembly 306. The blade assemblies 302, 304, and the support tube assembly 306, respectively, are normally pre-assembled prior to mounting to the handpiece 308 (e.g., the first tubular member 312 is assembled to the first hub 330 prior to assembling the first hub 330 to the handpiece 308). However, for purposes of clarification, the following description presents assembly of the surgical instrument 300 in terms of the tubular members 312, 316, 309 as being separate from the corresponding hubs 330, 350, 392. With reference to FIGS. 8A-8C, assembly of the surgical cutting instrument 300 includes coupling the motor 432 to the drive coupling 434 within the housing 430. In particular, the drive shaft 440 is connected to the output shaft 444 via the drive ring 442 and the teeth 452 such that the output shaft 444 rotates with rotation of the drive shaft 440. Further, the passage 454 of the output shaft 444 is fluidly connected to the aspiration port 438. The first hub 330 is sealingly mounted to the output shaft 444 such that the passages 338, 454 are in fluid communication. In one embodiment, the first hub 330 and the output shaft 444 define corresponding engagement features (referenced generally at 496) effectuating a lock between the hub 330 and the output shaft 444, with a spring 498 biasing the first hub 330 to the locked position. Regardless, the first hub 330 rotates with rotation of the output shaft 444.

The wheel actuator 470 and the shaft 472 are assembled to the housing 430 at the arm 478. The collet 480 is co-axially disposed within the first sleeve 454 such that the first sleeve 454 contacts the collet 480 adjacent the proximal end 482 thereof in a manner that allows the collet 480 to rotate relative to the first sleeve 454. The first capture ring 450 is placed over the first sleeve 454 and mounts the first sleeve 454/collet 480 to the housing 430 via the threaded surface 458. In this regard, the first hub 330 is received within the channel 484 of the collet 480 such that the first hub 330 can rotate relative to the collet 480.

The second hub 350 is mounted to the collet 480, with the rib 389 of the second hub 350 nesting against the inner flange 488 of the collet 480. Further, individual ones of the ball bearings (not shown) are captured within the holes 490 of the collet 480, extending into respective ones of the detents 388 of the second hub 350. With this configuration, the second hub 350 is effectively locked to the collet 480 such that the second hub 350 rotates with rotation of the collet 480. Further, the central passageway 374 of the second hub 350 is aligned with the passage 338 of the first hub 330. With the one embodiment of FIG. 8C, a gap is established between the first hub 330 and the second hub 350 (such as with a cutting design in which the distal end of the first tubular member 312 interiorly abuts the distal end of the second tubular member 316). Alternatively, with other blade designs (e.g., burring), the first hub 330 bears against the ring 387 otherwise assembled to the proximal portion 370 of the second hub 350. Regardless, the second set of gear teeth 476, otherwise provided on the collet 480 with the one embodiment of FIGS. 8A-8C, mesh with the first set of gear teeth 474.

The irrigation hub 420 is assembled over the distal portion 372 of the second hub 350 such that the irrigation pathway 426 is fluidly connected to the irrigation passageway 376 of the second hub 350 via the circumferential groove 382. In one embodiment, O-rings (not shown) are placed within the slots 384, 386, respectively, and seal the second hub 350 relative to the irrigation hub 420 proximal and distal the circumferential groove 382. The irrigation hub 420 is further supported relative to the second hub 350 via the second sleeve 456, that otherwise abuts the first sleeve 454, via the second capture ring 452 that is connected to the second sleeve 456 at the threaded surface 459. Finally, the third hub 392 is mounted to the irrigation hub 420 by an adhesive or other acceptable mounting technique.

As best shown in FIG. 8A, the proximal section 332 of the first tubular member 312 is mounted to the first hub 330, with the central lumen 336 of the first tubular member 312 being fluidly connected to the passage 454 of the coupling hub 444. The proximal region 352 of the second tubular member 316 is mounted to the second hub 350, with the first tubular member 312 extending co-axially within the second tubular member 316. In one embodiment and with additional reference to FIG. 8B, a gasket (not shown) is placed about the first tubular member 312 within the proximal portion 370 of the second hub 350 to seal the open end 360 of the second tubular member 316 relative to an exterior of the first tubular member 312. In this regard, the radial passage 358 of the second tubular member 316 is fluidly aligned with the irrigation passageway 376 of the second hub 350 such that the lumen 356 of the second tubular member 316 is fluidly connected with the irrigation pathway 426 defined by the irrigation port 422. Finally, the proximal portion 394 of the third tubular member 390 is mounted to the third hub 392. The second tubular member 316 is co-axially disposed within the third tubular member 390. As previously described, the first and second tubular members 312, 316 conform to the bend B defined by the third tubular member 390.

Upon final assembly, the distal end 400 of the third tubular member 390 terminates proximal the cutting tip 314 and the cutting window 318. That is to say, the cutting tip 314 and the cutting window 318 are distally exposed relative to the third tubular member 390.

Figure 9A:
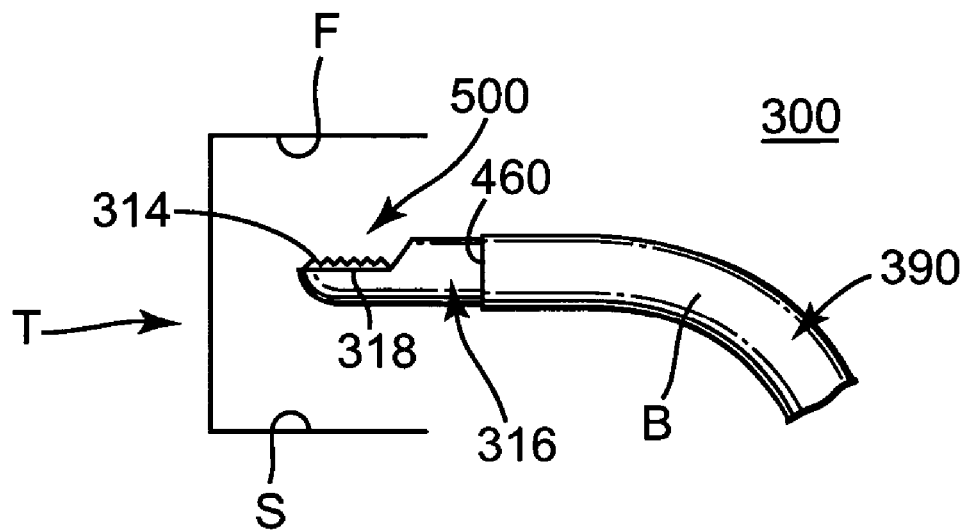
FIGS. 9A and 9B are simplified, side views of a portion of the instrument of FIG. 7 deployed at a target site illustrating use of the instrument.
Figure 9B:
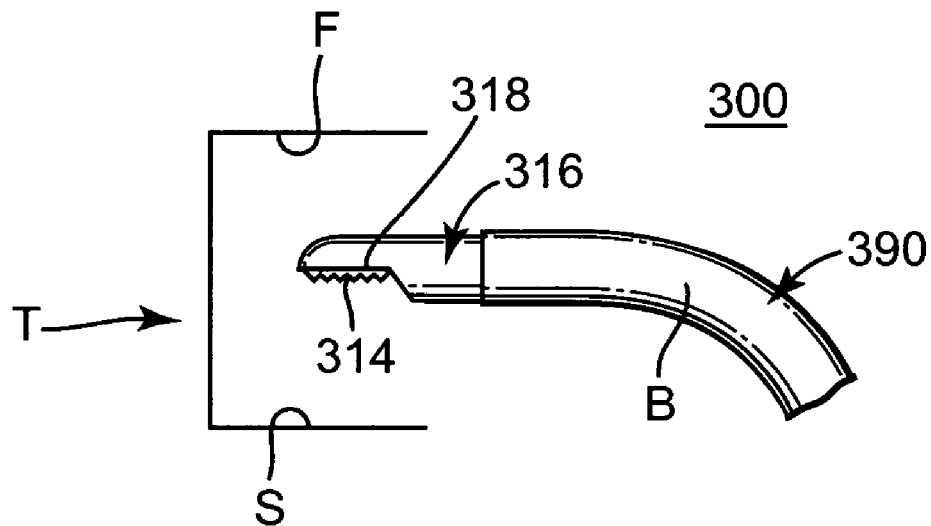

During use, the surgical cutting instrument 300 operates in a manner highly similar to that previously described with respect to the surgical cutting instrument 30 (FIG. 1). A user (not shown) grasps the handpiece 308 and guides the cutting tip 314/cutting window 318 (collectively referred to as the cutting implement 500) to a target site T as shown in FIG. 9A. The bend B in the third tubular member 390 facilitates convenient delivery of the cutting implement 500 to the target site T. As shown in FIG. 9A, upon initial delivery to the target site T, the cutting window 318 faces or is open to a first surface F of the target site T. The surgical cutting instrument 300 can then be operated to remove tissue from the first surface F such as by rotating or oscillating the cutting tip 314 within the cutting window 318 (it being noted that for purposes of illustration, the cutting window 318 of the second tubular member 316 is shown without the serrated edges in FIGS. 9A and 9B). Where desired, removal of tissue at a second surface S of the target site T can similarly be performed by the surgical cutting instrument 300. To this end, with the spatial orientation of FIG. 9A, the cutting window 318 is opposite or closed relative to the second surface S. Thus, the cutting window 318 must be spatially rotated relative to the target site T. The surgical cutting instrument 300 facilitates this change in spatial orientation in a manner by which the user is not required to use both hands, and achieves spatial rotation of the cutting window 318 relative to the handpiece 308.

In particular, and with additional reference to FIG. 8B, the wheel actuator 470 is manipulated by the user's thumb and/or index finger of the hand that is otherwise grasping the housing 430. Rotation of the wheel actuator 470 is translated to rotation of the second hub 350 via the actuator assembly 310. In particular, rotation of the thumb wheel actuator 470 rotates the shaft 472 that correspondingly rotates the first set of gear teeth 474. The first set of gear teeth 474 meshes with the second set of gear teeth 476 otherwise provided by the collet 480. Interface between the gear teeth 474, 476 is transferred to the collet 480, causing the collet 480 to rotate. The collet 480, in turn, rotates the second hub 350 that in turn effectuates rotation of the second tubular member 316. As a result, rotation of the wheel actuator 470 rotates the cutting window 318 relative to the handpiece 308. Notably, the third tubular member 390 maintains its spatial positioning relative to the handpiece 308 during rotation of the second tubular member 316. More particularly, the second tubular member 316 rotates within the third tubular member 390 such that a spatial location of the bend B remains stationary. The wheel actuator 470 is further manipulated until the cutting window 318 assumes the spatial orientation shown in FIG. 9B. Subsequently, the surgical cutting instrument 300 can be operated to facilitate interaction between the cutting implement 500 and tissue at the second surface S.

With conventional surgical cutting instruments incorporating a curved or bent blade assembly, changing the spatial orientation of the cutting window relative to the target site T normally requires that the blade assembly be removed from the target site and replaced with a different blade assembly having a cutting window orientation conducive to performing the desired cutting operation and/or repositioning the handpiece in the surgeon's hand prior to re-insertion of the blade assembly. Where an IGS system is also employed, re-registration of the cutting tip is required. The surgical instrument 300 of the present invention overcomes this concern. In particular, upon placement of the cutting implement 500 at the target site T as shown in FIG. 9A, the cutting implement 500 is registered relative to a visualization system (not shown). This registration remains in tact as the cutting window 318 is subsequently maneuvered to the spatial orientation of FIG. 9B. In other words, the cutting window 318 spatial orientation can be changed without removal of the cutting implement 500 from the target site T such that re-registration is not required.

The above-described surgical cutting instrument 300 is highly conducive for use with a curved blade configuration. Alternatively, the tubular members 312, 316 can be straight or linear. Notably, with a straight configuration, the support tube 390 (FIG. 8A) can be eliminated.

Figure 10:
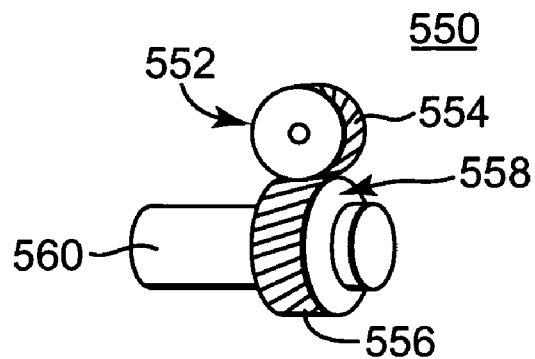
FIG. 10 is a side view of an alternative embodiment actuator assembly for use with the surgical cutting instrument in accordance with the present invention.

The previously described surgical cutting instruments 30 (FIG. 2), 300 (FIG. 7) have each described an actuator assembly employing a wheel actuator (such as the wheel actuator 180 of FIG. 2A) rotating about an axis that is perpendicular to an axis of the tubular member being rotated. Alternative actuator assembly configurations are equally acceptable and are within the scope of the present invention. For example, FIG. 10 illustrates an alternative actuator assembly 550 useful with the previously described surgical cutting instruments 30, 300. The actuator assembly 550 includes an actuator 552, a first set of gear teeth 554, and a second set of gear teeth 556. The actuator 552 associated with the embodiment of FIG. 10 is a wheel and forms the first set of gear teeth 554 along an outer circumference thereof. The second set of gear teeth 556 mesh with the first set of gear teeth 554, defining a worm gear configuration. With the one embodiment of FIG. 10, the second set of gear teeth 556 are formed on a ring 558 that is otherwise mounted to a collet 560. The collet 560 is akin to the collet 480 (FIG. 8B) previously described. Alternatively, with respect to the surgical cutting instrument 30 of FIG. 2, the second set of gear teeth 556 can be formed by, or attached to, the second hub 90 (FIG. 3B). Regardless, the wheel actuator 552 is secured to the surgical cutting instrument housing (e.g., the housing 130 of FIG. 3A or the housing 430 of FIG. 8A) such that the user's thumb and/or index finger (not shown) can readily access and rotate the wheel actuator 552. Rotation of the wheel actuator 552, in turn, results in rotation of the collet 560 via interaction between the first and second sets of gear teeth 554, 556. Rotation of the collet 560, in turn, results in rotation of a desired hub (such as the second hub 350 of FIG. 8A).

Figure 11:
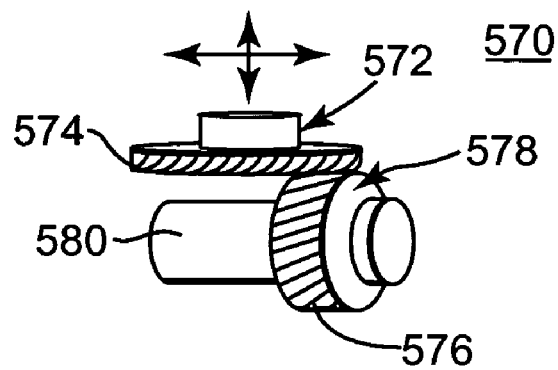
FIG. 11 is a side view of another alternative embodiment actuator assembly for use with the surgical cutting instrument of the present invention.

Yet another alternative embodiment actuator assembly 570 useful with the present invention is shown in FIG. 11. The actuator assembly 570 includes an actuator 572, a first set of gear teeth 574, and a second set of gear teeth 576. With the embodiment of FIG. 11, the actuator 572 is a slide coupled to the housing (such as the housing 430 of FIG. 8A) such that the slide actuator 572 can move horizontally and vertically (relative to the orientation of FIG. 11). The first set of gear teeth 574 are formed on the finger slide actuator 572. The second set of gear teeth 576 meshingly engage the first set of gear teeth 574. In this regard, and in one embodiment, the second set of gear teeth 576 are formed by a ring 578 that is otherwise attached to a collet 580. The collet 580 is akin to the collet 480 (FIG. 8B) previously described and is mounted to a hub (not shown). Alternatively, the second set of gear teeth 576 can be formed by, or directly attached to, the hub of interest (such as the second hub 90 associated with the surgical cutting instrument 30 of FIG. 3A). Regardless, horizontal movement (i.e., left-to-right or right-to-left relative to the orientation of FIG. 11) causes the first set of gear teeth 574 to slide within a gap defined between adjacent ones of the second set of gear teeth 576. Due to the angular orientation of the second set of gear teeth 576 relative to a central axis of the ring 578, horizontal or axial movement of the slide actuator 572 thus causes the ring 578 to rotate. Rotation of the ring 578 is imparted onto the collet 580 that in turn causes a hub (not shown) connected thereto to rotate. The slide actuator 572 can be horizontally lifted from a first gap and repositioned or indexed within another gap formed between different adjacent ones of the second set of gear teeth 576 to allow for continued rotation.

Figure 12:
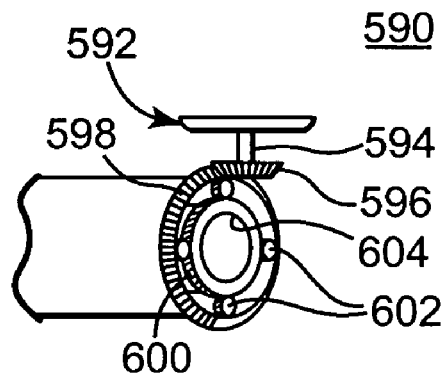
FIG. 12 is a side view of another alternative embodiment actuator assembly for use with the surgical cutting instrument of the present invention.

Yet another alternative embodiment actuator assembly 590 useful with the present invention is shown in FIG. 12. The actuator assembly 590 includes an actuator 592, a shaft 594, a first set of gear teeth 596, a second set of gear teeth 598, a third set of gear teeth 600, and planetary gears 602. With the embodiment of FIG. 12, the actuator 592 is a thumb wheel. The shaft 594 extends from a central axis of the thumb wheel actuator 592, with the first set of gear teeth 596 being formed by, or attached to, the shaft 594 opposite the thumb wheel actuator 592. The first set of gear teeth 596 mesh with the second set of gear teeth 598 that are otherwise formed on a ring 604. The third set of gear teeth 600 are indirectly coupled to the second set of gear teeth 598 via the planetary gears 602. Further, the third set of gear teeth 600 are formed by, or attached to, a hub 604 (such as the second hub 90 of FIG. 3A) or collet (such as the collet 480 of FIG. 8A) of interest. With the configuration of FIG. 12, a reduction in the gear ratio is achieved to further enhance a user's ability to effectuate cutting window spatial rotation.

Figure 13:
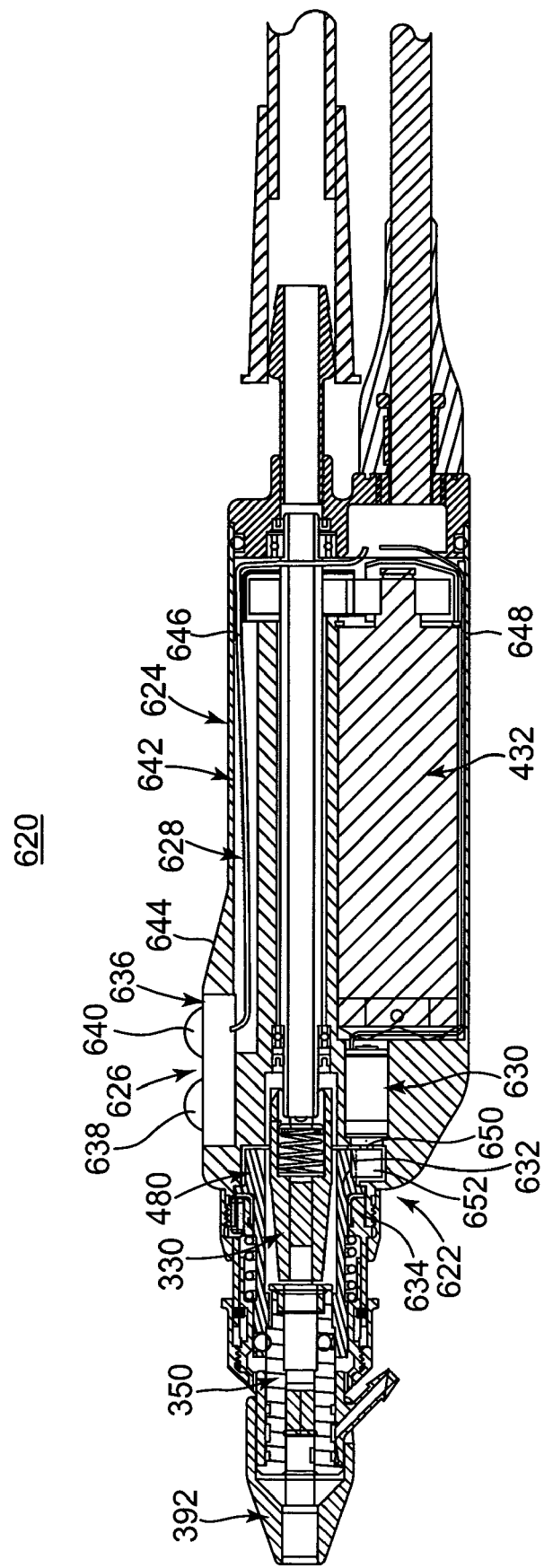
FIG. 13 is a cross-sectional view of a surgical cutting instrument in accordance with the present invention incorporating an alternative embodiment actuator assembly.

FIG. 13 illustrates a portion of an alternative embodiment surgical cutting instrument 620 including an alternative embodiment actuator assembly 622 (referenced generally) within the scope of the present invention. The surgical cutting instrument 620 is highly similar to the surgical cutting instrument 300 (FIG. 8A) previously described, with like elements being similarly numbered. Further, for ease of illustration, the surgical cutting instrument 620 is shown with the tubular members and support tube removed. With this in mind, the surgical cutting instrument 620 generally includes the actuator assembly 622, a housing 624, the first hub 330, the second hub 350, and the third hub 392. The actuator assembly 622 includes a switch mechanism 626, wiring 628, a secondary motor 630, a first set of gear teeth 632, and a second set of gear teeth 634. In general terms, the wiring 628 electrically connects the switch mechanism 626 to the motor 630. Operation of the motor 630 causes the first set of gear teeth 632 to rotate. The second set of gear teeth 634 meshingly engage the first set of gear teeth 632, and are attached to, or formed by, the collet 480. As previously described, rotation of the collet 480, in turn, rotates the second hub 350 resulting in rotation of the cutting window 318 (FIG. 8A) relative to the housing 624.

The switch mechanism 626 can assume a variety of forms, and preferably is sealed relative to the housing 624. In one embodiment, the switch mechanism 626 includes a keypad 636 having first and second keys or buttons 638, 640. With this one configuration, actuation of the first button 638 causes the motor 630 to rotate in a first direction whereas actuation of the second button 640 causes the motor 630 to rotate in an opposite direction. Regardless, the keypad 636 is preferably formed on an exterior 642 of the housing 624, and is located so as to be readily accessible by a user's hand (not shown) that is otherwise naturally grasping the housing 624. In other words, the housing 624 provides a natural orientation whereby the user's palm (not shown) is placed at a top side 644 (relative to the orientation of FIG. 13). With this in mind, the keypad 636 is preferably located along the top side 644 so as to readily facilitate interface thereof with the user's thumb and/or index finger of the hand that is otherwise grasping the housing 624. Alternatively, other configurations for the switch mechanism 626 are equally acceptable.

As previously described, the wiring 628 electrically connects the switch mechanism 626 to the motor 630. In one embodiment, the wiring 628 provides an indirect connection by including a first wiring segment 646 extending from the switch mechanism 626 to a discreet control device (not shown) located apart from the housing 624, and a second wiring segment 648 extending from the control device to the motor 630. Alternatively, the wiring 628 can directly connect the switch mechanism to the motor 630.

The secondary motor 630 is maintained within the housing 624, and is separate from the primary motor 432 otherwise operated to rotate the first hub 330. With this in mind, the motor 630 can assume a variety of forms, and operates to rotate a drive shaft 650. The first set of gear teeth 632 are formed on the drive shaft 650. In one embodiment, the second set of gear teeth 634 are formed on the collet 480 as previously described. A dynamic seal 652 is preferably formed between the first set of gear teeth 632 and the motor 630 so as to seal the motor 630 relative to the housing 624.

During use, the surgical cutting instrument 620 operates in a manner highly similar to that previously described. When desired, the switch mechanism 626 is operated to effectuate a change in spatial orientation of the cutting window (not shown) relative to the housing 624. As with previous embodiments, a user can accomplish this change in cutting window orientation using only a single hand and without rotational movement of the housing 624.

The surgical cutting instrument and related method of use of the present invention provides a marked improvement over previous designs. In particular, rotation of a cutting window relative to a handpiece and target site is readily accomplished by a user without requiring both of the user's hands. To this end, with each of the embodiments shown, including each of the actuator assemblies described, a primary actuator is moved by the user in a first direction and/or about a rotational axis. This movement is translated to the hub that otherwise maintains the tubular member forming the cutting window, with this hub having a hub axis. The actuator assembly is such that the actuator movement is not co-axial with the hub axis, thereby eliminating the need for both hands of the user to effectuate a change in cutting window positioning. In one embodiment, the blade assemblies define a curve, with the surgical cutting instrument adapted to effectuate cutting window rotation relative to the handpiece (and the target site) without altering a spatial location of the bend.

The surgical cutting instrument, and in particular the surgical cutting instrument 300 and other similar designs incorporating a bent tube in conjunction with a spatially rotatable window, is highly useful for a number of surgical procedures. For example, the surgical cutting instrument can readily be used for an uncinectomy and maxillary sinus antrostomy in which the cutting window is repositioned (without requiring overt movement of the handpiece and/or removal of the cutting implement from the target site) to access the antrostomy superiorly, inferiorly, and posteriorly. Similarly, the surgical cutting instrument of the present invention is well-suited for maxillary polypectomy or removal of fungus, cysts, or other pathology in the maxillary sinus, either through the maxillary antrostomy or through an anterior maxillary trephination. The surgical cutting instrument is also useful with lateral and medial frontal sinusotomy procedures in which the rotatable cutting window allows cutting laterally, medially, and posteriorly. Other surgical procedures with which the surgical cutting instrument of the present invention is useful include acoustic neuroma, debulking of laryngeal, tracheal, and bronchial lesions, and spinal disc space nucleostomy, to name but a few.

Although the present invention has been described with reference to preferred embodiments, workers skilled in the art will recognize that changes can be made in form and detail without departing from the spirit and scope of the present invention.

What is claimed is:
1. A surgical cutting instrument comprising:
 a first elongated member having a proximal section and a distal section having a cutting tip;
 a second tubular member having a proximal region and a distal region forming a cutting window, wherein the first elongated member is co-axially disposed within the second tubular member such that the cutting tip is exposed at the cutting window to cause cutting of tissue therebetween as the first elongated member rotates;
 a handpiece;

a first hub mounted to an exterior of the proximal section of the first elongated member and rotatably coupled to, and disposed entirely within, the handpiece;

a second hub mounted to the proximal region of the second tubular member and rotatably coupled to the handpiece, the second hub defining a hub axis; and an actuator assembly coupling the second hub to the handpiece, the actuator assembly including an actuator rotatably mounted to the handpiece such that a portion of the actuator is exteriorly exposed for manual interface by a user and rotates about a rotational axis;

wherein the actuator assembly is adapted to translate a movement of the actuator to a rotational movement of the second hub relative to the handpiece to effectuate spatial rotation of the cutting window, wherein the rotational axis is perpendicular to the hub axis.

2. The surgical cutting instrument of claim 1, wherein the actuator movement is an axial motion.

3. The surgical cutting instrument of claim 1, wherein the actuator assembly includes gear teeth.

4. The surgical cutting instrument of claim 1, wherein the actuator assembly further includes:

a first set of gear teeth connected to the second hub;

wherein the actuator movement is transferred to the first set of gear teeth to cause rotational movement of the second hub.

5. The surgical cutting instrument of claim 4, wherein the first set of gear teeth are mounted to the second hub.

6. The surgical cutting instrument of claim 4, wherein the actuator assembly further includes:

a second set of gear teeth meshingly engaged with the first set of gear teeth, the second set of gear teeth being connected to the actuator.

7. The surgical cutting instrument of claim 6, further comprising:

a collet rotatably coupled to the handpiece and capturing the second hub such that the second hub rotates with rotation of the collet;

wherein the first set of gear teeth are connected to the collet.

8. The surgical cutting instrument of claim 7, wherein the actuator is a wheel, the actuator assembly further comprising:

a shaft extending from the wheel to define the rotational axis and further wherein the shaft is connected to the second set of gear teeth.

9. The surgical cutting instrument of claim 8, wherein the second set of gear teeth are formed on the shaft opposite the wheel.

10. The surgical cutting instrument of claim 9, wherein the second set of gear teeth defines a bevel gear.

11. The surgical cutting instrument of claim 1, wherein the actuator assembly further includes a collet, the surgical cutting instrument further comprising:

an irrigation hub fluidly connected to a lumen of the second tubular member via the second hub;

wherein the collet couples the irrigation hub to the handpiece and the second hub is rotatably coupled to the irrigation hub.

12. The surgical cutting instrument of claim 1, wherein the actuator assembly further includes:

a collet coupled to the handpiece;

wherein the collet is coupled to the second hub such that the second hub rotates with rotation of the collet.

13. The surgical cutting instrument of claim 12, further comprising:

an irrigation port assembly including an irrigation port fluidly connected to the second hub.

14. The surgical cutting instrument of claim 13, wherein the second hub forms a central passage within which the second tubular member is received and an irrigation passageway fluidly connecting the central passage with an exterior of the second hub, and further wherein the irrigation port is fluidly connected to the irrigation passageway.

15. The surgical cutting instrument of claim 14, wherein the second tubular member forms a lumen and a radial passage fluidly connected to the lumen, and further wherein the radial passage is fluidly connected to the central passage of the second hub such that the irrigation port is fluidly connected to the lumen.

16. The surgical cutting instrument of claim 15, wherein the second hub is rotatable relative to the irrigation port assembly, and further wherein the second hub is adapted to maintain a fluid connection between the irrigation port and the irrigation passageway at any rotational position of the second hub relative to the irrigation port assembly.

17. The surgical cutting instrument of claim 12, further comprising:

a third tubular member having a proximal region and a distal region terminating in a distal end; and a third hub mounted to the proximal region of the third tubular member and coupled to the handpiece;

wherein the second tubular member is co-axially disposed within the third tubular member;

and further wherein upon final assembly, the cutting window of the second tubular member extends distal the distal end of the third tubular member.

18. The surgical cutting instrument of claim 17, wherein the third hub extends distal the second hub.

19. The surgical cutting instrument of claim 17, wherein the third hub is spatially fixed relative to the handpiece such that the third hub does not rotate relative to the handpiece.

20. The surgical cutting instrument of claim 17, wherein the second hub is rotatably mounted to the third hub.

21. The surgical cutting instrument of claim 17, wherein the third tubular member defines a bend along a longitudinal length thereof.

22. The surgical cutting instrument of claim 21, wherein the first elongated member and the second tubular member are adapted to conform to the bend defined by the third tubular member.

23. The surgical cutting instrument of claim 22, wherein the instrument is adapted such that the third hub remains fixed with rotation of the second hub such that the bend remains spatially fixed upon rotation of the second tubular member.

24. The surgical cutting instrument of claim 17, further comprising:

a coating on an exterior of the second tubular member for minimizing movement of the second tubular member relative to the third tubular member with rotation of the first tubular member relative to the second tubular member.

25. The surgical cutting instrument of claim 24, wherein the coating is shrink tubing.

26. The surgical cutting instrument of claim 12, wherein the collet, the first hub, and the second hub are co-axial.

27. The surgical cutting instrument of claim 12, wherein a portion of the first hub and a portion of the second hub are disposed within the collet.

28. The surgical cutting instrument of claim 1, wherein the first tubular elongated member is a tube.

29. The surgical cutting instrument of claim 1, wherein the handpiece includes a housing having a top side and a bottom side that collectively define a contour adapted to promote placement of the top side in a user's palm, and further wherein the actuator is positioned along the top side of the housing.

30. The surgical cutting instrument of claim 1, wherein the cutting tip is selected from the group consisting of a serrated edge and a bur.

31. The surgical cutting instrument of claim 1, wherein the handpiece includes a housing maintaining a motor, the motor being separate from the actuator assembly and coupled to the first hub such that the motor is operable to cause rotation of the first member in performing a cutting operation.

32. A surgical cutting instrument comprising:
- a first elongated member having a proximal section and a distal section having a cutting tip;
- a second tubular member having a proximal region and a distal region forming a cutting window, wherein the first elongated member is co-axially disposed within the second tubular member such that the cutting tip is exposed at the cutting window, wherein the cutting tip is not exposed distal the cutting window;
- a third tubular member having a proximal region and a distal region terminating in a distal end, the third tubular member forming a bend along a longitudinal length thereof, wherein the second tubular member is disposed within the third tubular member and the cutting window is distal the distal end;
- wherein the first elongated member and the second tubular member are adapted to conform to the bend defined by the third tubular member;
- a handpiece;
- a first hub mounted to the proximal section of the first elongated member and moveably coupled to the handpiece;
- a second hub mounted to the proximal region of the second tubular member and rotatably coupled to the handpiece about a hub axis;
- a third hub mounted to the proximal region of the third tubular member and coupled to the handpiece;
- wherein upon final assembly, the second hub is rotatable relative to the third hub; and
- an actuator assembly coupling the second hub to the handpiece and including an actuator, the actuator assembly adapted to translate a movement of the actuator to a rotational movement of the second hub relative to the handpiece and the third hub to effectuate spatial rotation of the cutting window.

33. The surgical cutting instrument of claim 32, further comprising:
- an irrigation port assembly including an irrigation hub and an irrigation port;
- wherein the second hub is disposed within the irrigation hub and the irrigation port is fluidly connected to a central passage of the second hub.

34. The surgical cutting instrument of claim 33, wherein the irrigation hub is disposed between the third hub and the second hub.

35. The surgical cutting instrument of claim 34, wherein the irrigation port projects exteriorly beyond the third hub.

36. The surgical cutting instrument of claim 33, wherein upon final assembly, the second hub is rotatable relative to the irrigation hub with movement of the actuator.

37. The surgical cutting instrument of claim 32, further comprising:
- a shaft extending from the actuator; and
- a collet coupling the shaft to the second hub;
- wherein the actuator is a thumb wheel having a perimeter that is exteriorly accessible by a user relative to the handpiece such that rotation of the thumb wheel is translated to the second hub via the shaft and the collet.

38. The surgical cutting instrument of claim 37, wherein the first hub is co-axially disposed within the collet.

* * * * *